(12) United States Patent
Denzinger et al.

(10) Patent No.: US 11,419,605 B2
(45) Date of Patent: Aug. 23, 2022

(54) APPARATUS AND METHOD TO CLOSE END EFFECTOR OF SURGICAL STAPLER ONTO BUTTRESS

(71) Applicant: Ethicon LLC, Guaynabo, PR (US)

(72) Inventors: Christopher A. Denzinger, Cincinnati, OH (US); Heather Strang, West Chester, OH (US); Michael J. Vendely, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/022,414

(22) Filed: Sep. 16, 2020

(65) Prior Publication Data
US 2022/0079583 A1  Mar. 17, 2022

(51) Int. Cl.
*A61B 17/068* (2006.01)
*A61B 17/072* (2006.01)
*A61B 17/00* (2006.01)

(52) U.S. Cl.
CPC ........ *A61B 17/0686* (2013.01); *A61B 17/072* (2013.01); *A61B 2017/00336* (2013.01);
(Continued)

(58) Field of Classification Search
CPC ..... A61B 17/04; A61B 17/0401; A61B 17/28; A61B 17/2825; A61B 17/29;
(Continued)

(56) References Cited

U.S. PATENT DOCUMENTS

| 4,930,674 A | 6/1990 | Barak |
| 5,358,510 A | 10/1994 | Luscombe et al. |

(Continued)

FOREIGN PATENT DOCUMENTS

| EP | 2 090 248 A2 | 8/2009 |
| EP | 3 072 460 A2 | 9/2016 |

(Continued)

OTHER PUBLICATIONS

U.S. Appl. No. 17/022,186, entitled "Apparatus and Method to Apply Buttress to End Effector of Surgical Stapler via Fixed Base," filed Sep. 16, 2020.

(Continued)

*Primary Examiner* — Stephen F. Gerrity
*Assistant Examiner* — Linda J Hodge
(74) *Attorney, Agent, or Firm* — Frost Brown Todd LLC

(57) ABSTRACT

An apparatus is provided for applying an adjunct element to at least one of opposing first and second jaws of an end effector of a surgical stapler, wherein each of the first and second jaws includes a stapling surface and an external surface opposed from the respective stapling surface. The apparatus comprises: (a) a platform configured to be positioned between the first and second jaws of the end effector; (b) an adjunct element positioned on the platform; and (c) at least one closure surface opposed from the platform, wherein the at least one closure surface is configured to mechanically engage the external surface of at least one of the first or second jaws to thereby transition the end effector from an open state toward a closed state for placing the respective stapling surface of the at least one of the first or second jaws in contact with the adjunct element.

20 Claims, 25 Drawing Sheets

(52) U.S. Cl.
CPC .............. *A61B 2017/07257* (2013.01); *A61B 2017/07271* (2013.01)

(58) Field of Classification Search
CPC .. A61B 17/2829; A61B 17/068–07207; A61B 17/07292; A61B 2017/07257; A61B 2017/07271; A61B 2017/00336; A61B 2017/0406; B25B 5/067; B25B 27/00; B23P 11/00; B23P 11/005
USPC ........... 227/175.1–182.1; 606/148, 151, 154; 29/244, 278, 276; 269/143, 249
See application file for complete search history.

(56) References Cited

U.S. PATENT DOCUMENTS

| | | | |
|---|---|---|---|
| 5,372,868 | A | 12/1994 | Prewo et al. |
| 5,655,698 | A | 8/1997 | Yoon |
| 5,697,542 | A | 12/1997 | Knodel et al. |
| 5,752,965 | A | 5/1998 | Francis et al. |
| 5,769,892 | A | 6/1998 | Kingwell |
| 5,810,855 | A | 9/1998 | Rayburn et al. |
| 5,833,695 | A | 11/1998 | Yoon |
| 5,901,895 | A | 5/1999 | Heaton et al. |
| 5,902,312 | A | 5/1999 | Frater et al. |
| 6,019,791 | A | 2/2000 | Wood |
| 6,099,551 | A | 8/2000 | Gabbay |
| 6,273,897 | B1 | 8/2001 | Dalessandro et al. |
| 6,325,810 | B1 | 12/2001 | Hamilton et al. |
| 6,592,597 | B2 | 7/2003 | Grant et al. |
| 6,638,285 | B2 | 10/2003 | Gabbay |
| 7,147,138 | B2 | 12/2006 | Shelton, IV |
| 7,377,928 | B2 | 5/2008 | Zubik et al. |
| 7,380,696 | B2 | 6/2008 | Shelton, IV et al. |
| 7,559,937 | B2 | 7/2009 | De La Torre et al. |
| 7,665,646 | B2 | 2/2010 | Prommersberger |
| 7,708,180 | B2 | 5/2010 | Murray et al. |
| 7,845,533 | B2 | 12/2010 | Marczyk et al. |
| 8,052,697 | B2 * | 11/2011 | Phillips ................ A61B 17/122 606/151 |
| 8,210,411 | B2 | 7/2012 | Yates et al. |
| 8,348,130 | B2 | 1/2013 | Shah et al. |
| 8,408,439 | B2 | 4/2013 | Huang et al. |
| 8,453,914 | B2 | 6/2013 | Laurent et al. |
| 8,464,925 | B2 | 6/2013 | Hull et al. |
| 8,864,009 | B2 | 10/2014 | Shelton, IV et al. |
| 9,186,142 | B2 | 11/2015 | Fanelli et al. |
| 9,220,501 | B2 | 12/2015 | Baxter, III et al. |
| 9,517,065 | B2 | 12/2016 | Simms et al. |
| 9,622,746 | B2 | 4/2017 | Simms et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,421 | B2 | 12/2017 | Zerkle et al. |
| 9,999,408 | B2 | 6/2018 | Boudreaux et al. |
| 10,092,292 | B2 | 10/2018 | Boudreaux et al. |
| 10,166,023 | B2 | 1/2019 | Vendely et al. |
| 10,213,198 | B2 | 2/2019 | Aronhalt et al. |
| 10,349,939 | B2 | 7/2019 | Shelton, IV et al. |
| 10,932,779 | B2 | 3/2021 | Vendely et al. |
| 10,993,716 | B2 | 5/2021 | Shelton, IV et al. |
| 11,033,269 | B2 | 6/2021 | Vendely et al. |
| 11,045,196 | B2 | 6/2021 | Olson et al. |
| 11,051,812 | B2 | 7/2021 | Hopkins et al. |
| 11,058,418 | B2 | 7/2021 | Shelton, IV et al. |
| 2005/0267325 | A1 | 12/2005 | Bouchier et al. |
| 2006/0173470 | A1 | 8/2006 | Oray et al. |
| 2007/0162056 | A1 | 7/2007 | Gerbi et al. |
| 2007/0179528 | A1 | 8/2007 | Soltz et al. |
| 2007/0246505 | A1 * | 10/2007 | Pace-Floridia ....... A61L 31/044 227/175.1 |
| 2008/0128469 | A1 | 6/2008 | Dalessandro et al. |
| 2008/0169329 | A1 | 7/2008 | Shelton et al. |
| 2008/0203134 | A1 | 8/2008 | Shah et al. |
| 2009/0001122 | A1 | 1/2009 | Prommersberger et al. |
| 2009/0084825 | A1 | 4/2009 | Larson |
| 2009/0206126 | A1 | 8/2009 | Huitema et al. |
| 2010/0087840 | A1 | 4/2010 | Ebersole et al. |
| 2010/0163598 | A1 | 7/2010 | Belzer |
| 2011/0017802 | A1 | 1/2011 | Ma et al. |
| 2011/0087279 | A1 | 4/2011 | Shah et al. |
| 2011/0248064 | A1 | 10/2011 | Marczyk |
| 2012/0018487 | A1 | 1/2012 | Bettuchi et al. |
| 2012/0080336 | A1 | 4/2012 | Shelton, IV et al. |
| 2012/0265154 | A1 | 10/2012 | Criscuolo et al. |
| 2013/0037596 | A1 | 2/2013 | Bear et al. |
| 2013/0075447 | A1 * | 3/2013 | Weisenburgh, II ......................... A61B 17/00491 227/176.1 |
| 2013/0146642 | A1 | 6/2013 | Shelton, IV et al. |
| 2013/0256378 | A1 | 10/2013 | Schmid et al. |
| 2014/0058194 | A1 | 2/2014 | Soletti et al. |
| 2014/0131418 | A1 | 5/2014 | Kostrzewski |
| 2014/0131419 | A1 | 5/2014 | Bettuchi |
| 2014/0158741 | A1 * | 6/2014 | Woodard, Jr. ..... A61B 17/0401 227/175.1 |
| 2014/0239036 | A1 * | 8/2014 | Zerkle .................. A61B 17/068 227/175.1 |
| 2014/0288386 | A1 | 9/2014 | Zand et al. |
| 2014/0291379 | A1 | 10/2014 | Schellin et al. |
| 2015/0041168 | A1 | 2/2015 | Dostinov |
| 2015/0076212 | A1 | 3/2015 | Shelton, IV |
| 2015/0351761 | A1 | 12/2015 | Shelton, IV et al. |
| 2017/0055980 | A1 | 3/2017 | Vendely et al. |
| 2017/0056016 | A1 * | 3/2017 | Barton ............. A61B 17/07292 |
| 2017/0056018 | A1 | 3/2017 | Zeiner et al. |
| 2017/0281181 | A1 | 10/2017 | Matonick et al. |
| 2017/0303952 | A1 | 10/2017 | Nativ et al. |
| 2018/0235617 | A1 | 8/2018 | Shelton, IV et al. |
| 2018/0235626 | A1 | 8/2018 | Shelton, IV et al. |
| 2019/0290267 | A1 | 9/2019 | Baxter, III et al. |
| 2019/0321044 | A1 | 10/2019 | Franklin, Sr. |
| 2020/0015817 | A1 | 1/2020 | Harris et al. |
| 2020/0205823 | A1 | 7/2020 | Vendely et al. |
| 2020/0205825 | A1 | 7/2020 | Vendely et al. |
| 2020/0261080 | A1 | 8/2020 | Bakos et al. |
| 2020/0281587 | A1 | 9/2020 | Schmid et al. |
| 2020/0405436 | A1 | 12/2020 | Shelton, IV et al. |

FOREIGN PATENT DOCUMENTS

| | | |
|---|---|---|
| EP | 3 632 342 A2 | 4/2020 |
| EP | 3 673 831 A2 | 7/2020 |

OTHER PUBLICATIONS

U.S. Appl. No. 17/022,209, entitled "Apparatus and Method to Apply Buttress to End Effector of Surgical Stapler via Driven Member," filed Sep. 16, 2020.
U.S. Appl. No. 17/022,214, entitled "Apparatus and Method to Apply Buttresses Separately to Jaws of End Effector of Surgical Stapler," filed Sep. 16, 2020.
U.S. Appl. No. 17/022,419, entitled "Apparatus and Method to Detect Full Seating of Buttress Applicator in End Effector of Surgical Stapler," filed Sep. 16, 2020.
U.S. Appl. No. 17/022,442, entitled "Apparatus and Method to Apply Buttress to End Effector of Surgical Stapler with Authentication," filed Sep. 16, 2020.
U.S. Appl. No. 17/022,520, entitled "Method of Applying Buttress to End Effector of Surgical Stapler," filed Sep. 16, 2020.
Gore Seamguard Bioabsorbable Staple Line Reinforcement, Configured for Endoscopic Surgical Staplers, Instructions for Use, Jun. 2019, 136 pgs.
International Search Report and Written Opinion dated Nov. 30, 2021 for Application No. PCT/IB2021/058337, 16 pgs.
International Search Report and Written Opinion dated Nov. 29, 2021 for Application No. PCT/IB2021/058165, 14 pgs.
International Search Report and Written Opinion dated Dec. 2, 2021 for Application No. PCT/IB2021/058414, 14 pgs.
International Search Report and Written Opinion dated Feb. 16, 2022 for Application No. PCT/IB2021/060163, 15 pgs.

(56) References Cited

OTHER PUBLICATIONS

International Search Report and Written Opinion dated Nov. 30, 2021 for Application No. PCT/IB2021/058396, 14 pgs.
International Search Report and Written Opinion dated Dec. 2, 2021 for Application No. PCT/IB2021/058412, 15 pgs.
International Search Report and Written Opinion dated Nov. 25, 2021 for Application No. PCT/IB2021/058400, 15 pgs.

* cited by examiner

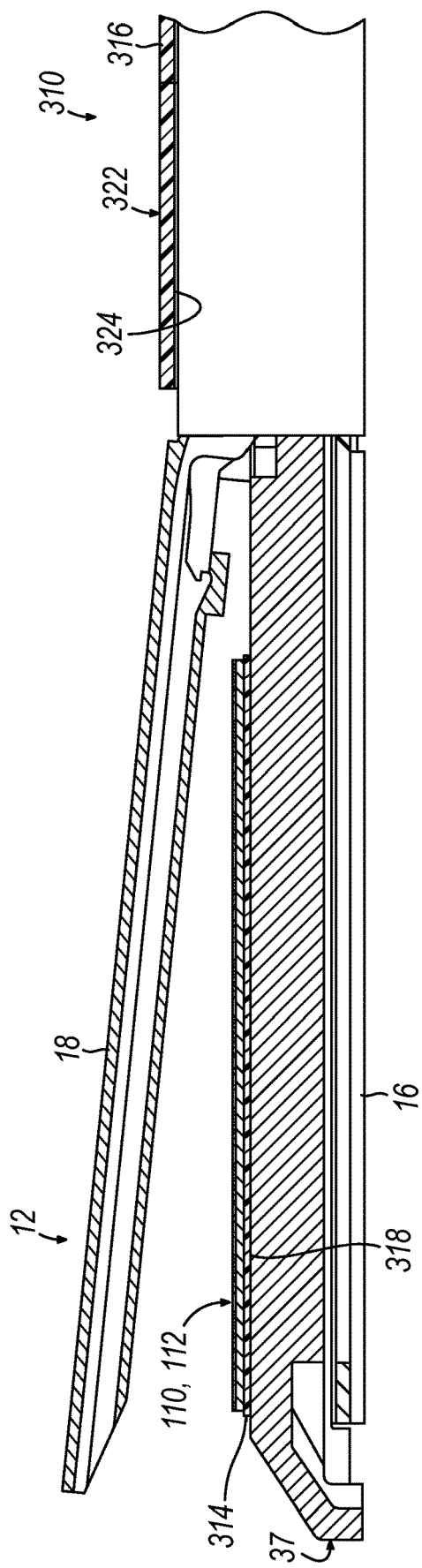
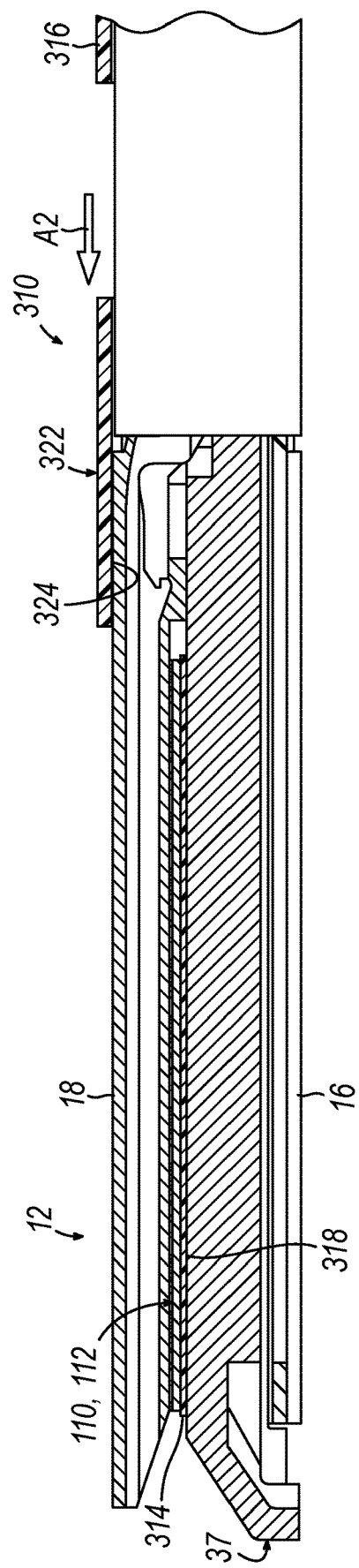
FIG. 15A
FIG. 15B

APPARATUS AND METHOD TO CLOSE END EFFECTOR OF SURGICAL STAPLER ONTO BUTTRESS

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 15A depicts a side cross-sectional view of the buttress applicator of FIG. 14 positioned over the end effector of FIG. 3, showing the translatable sleeve of the buttress applicator in the retracted position;

FIG. 15B depicts a side cross-sectional view of the buttress applicator of FIG. 14 positioned over the end effector of FIG. 3, showing the translatable sleeve of the buttress applicator in an extended position for transitioning the end effector toward the closed state;

Figure 1:
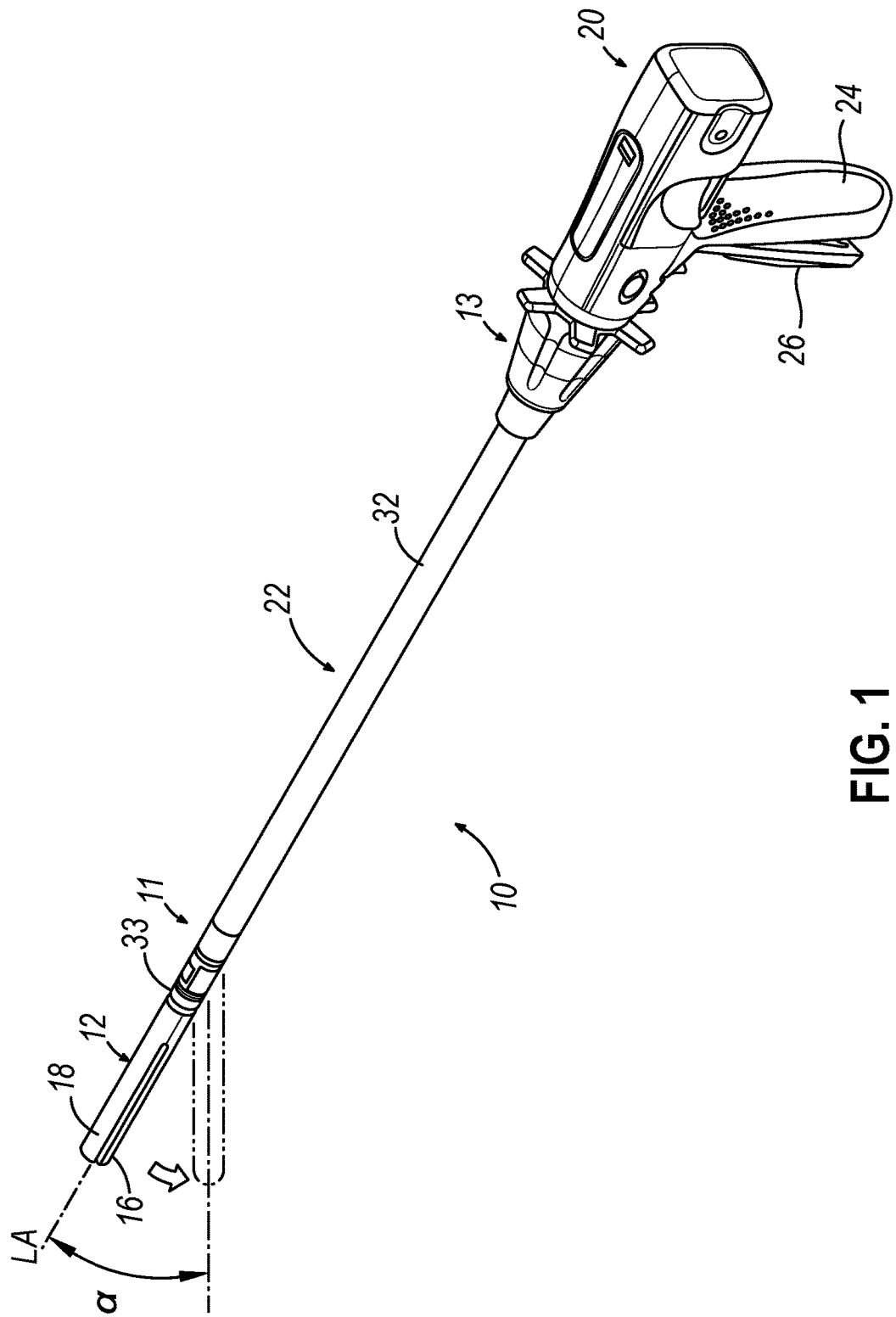
FIG. 1 depicts a perspective view of an exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

FIGS. 1-7 depict an exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) of the present example includes a lower jaw (16) that includes a staple cartridge (37), and an upper jaw in the form of a pivotable anvil (18).

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
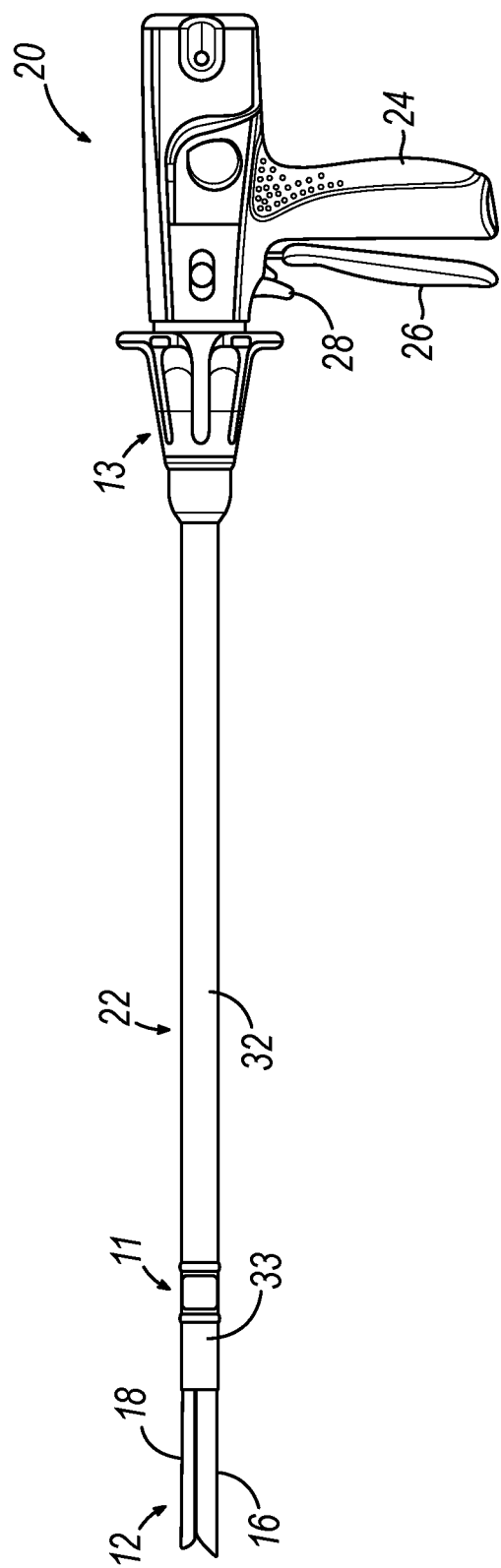
FIG. 2 depicts a side elevational view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44).

Figure 3:
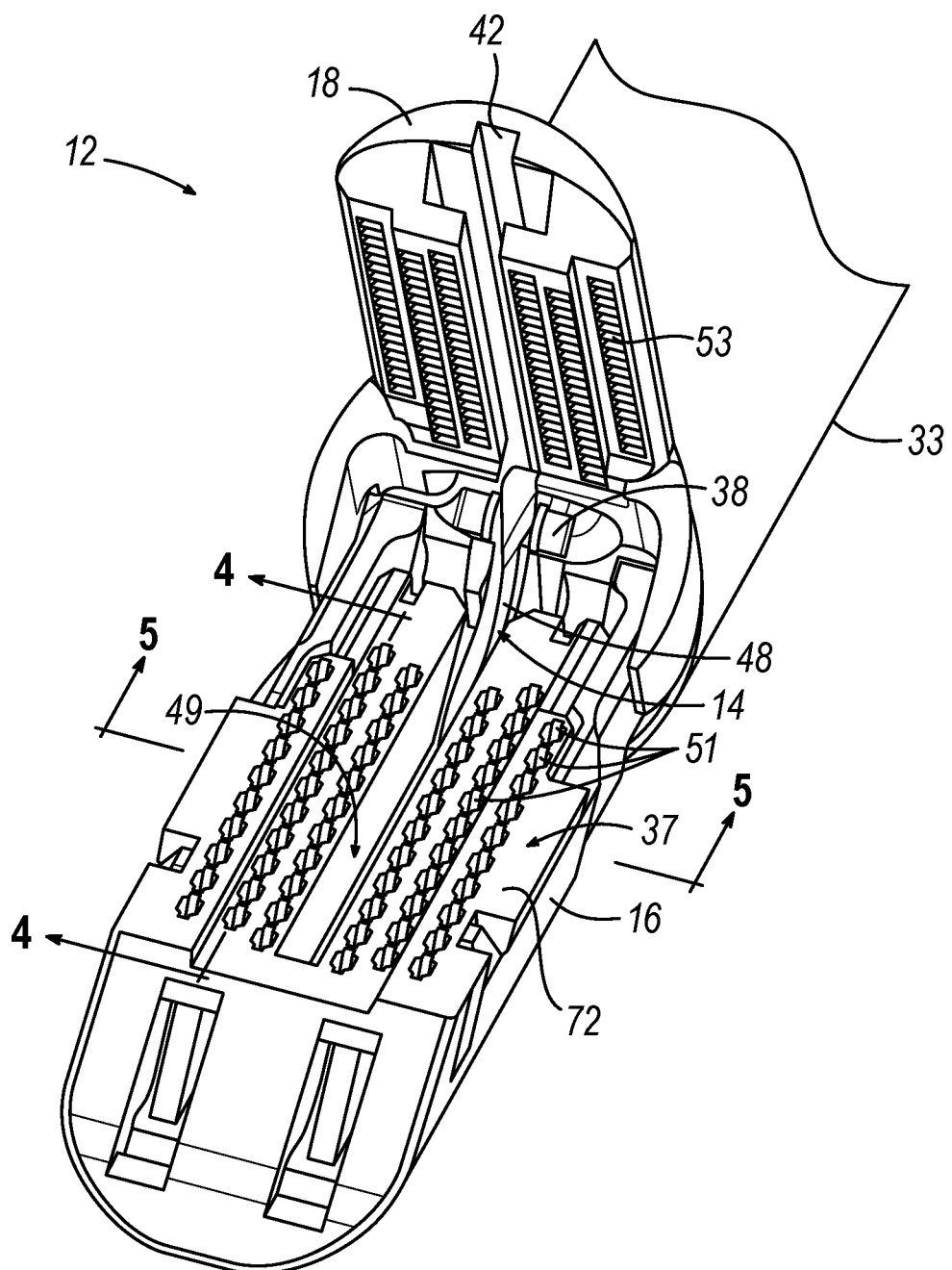
FIG. 3 depicts a perspective view of an end effector of the instrument of FIG. 1 in an open state.
Figure 4A:
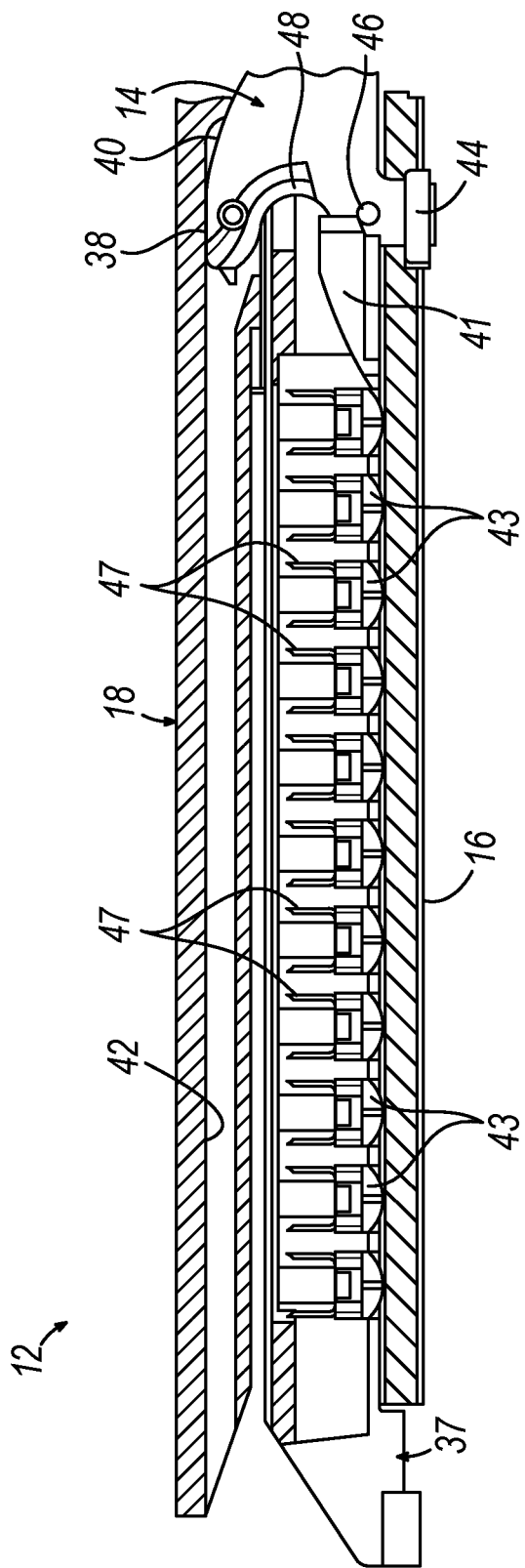
FIG. 4A depicts a side cross-sectional view of the end effector of FIG. 3, taken along line 4-4 of FIG. 3, with a firing beam in a proximal position.
Figure 4B:
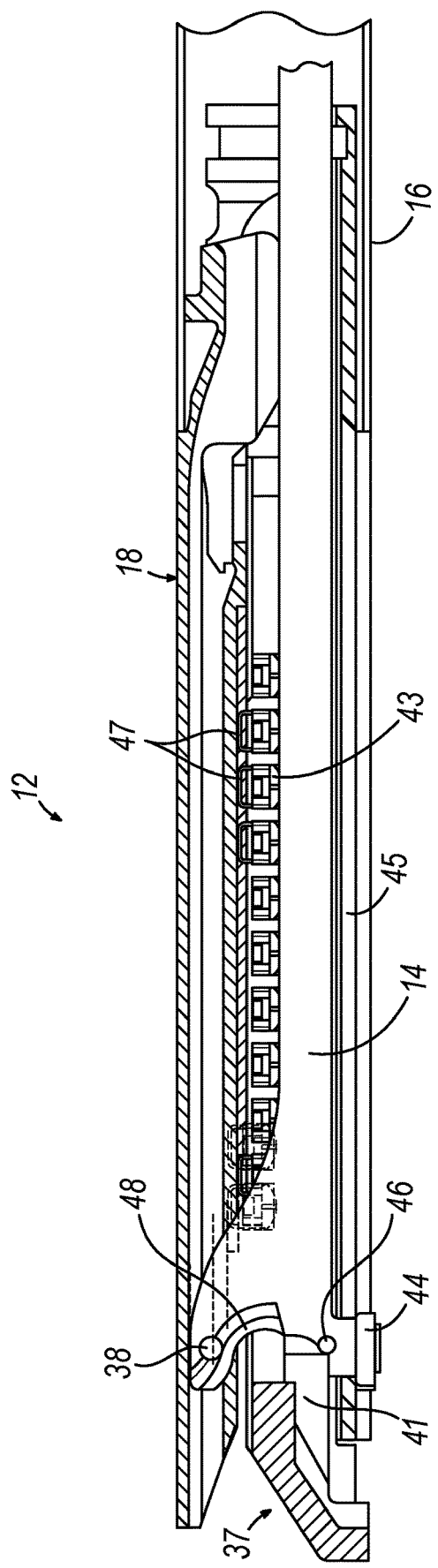
FIG. 4B depicts a side cross-sectional view of the end effector of FIG. 3, taken along line 4-4 of FIG. 3, with the firing beam in a distal position.
Figure 5:
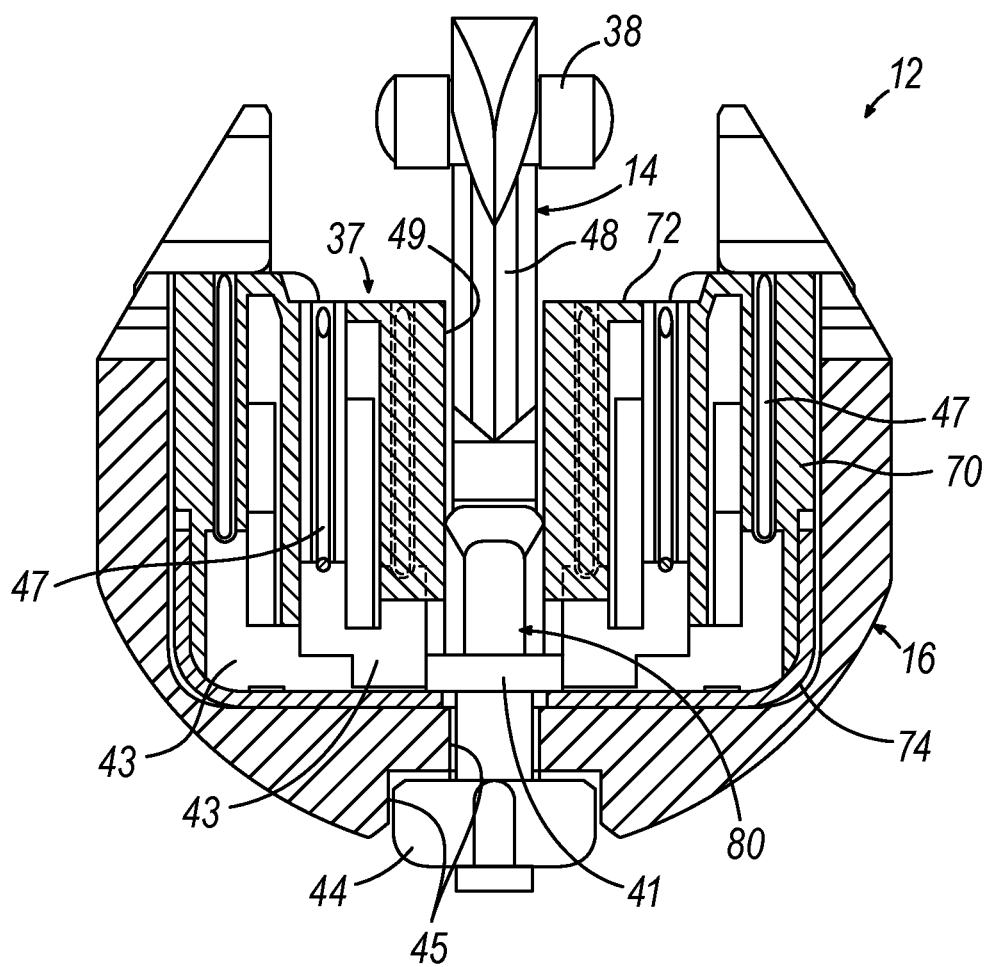
FIG. 5 depicts an end cross-sectional view of the end effector of FIG. 3, taken along line 5-5 of FIG. 3.
Figure 6:
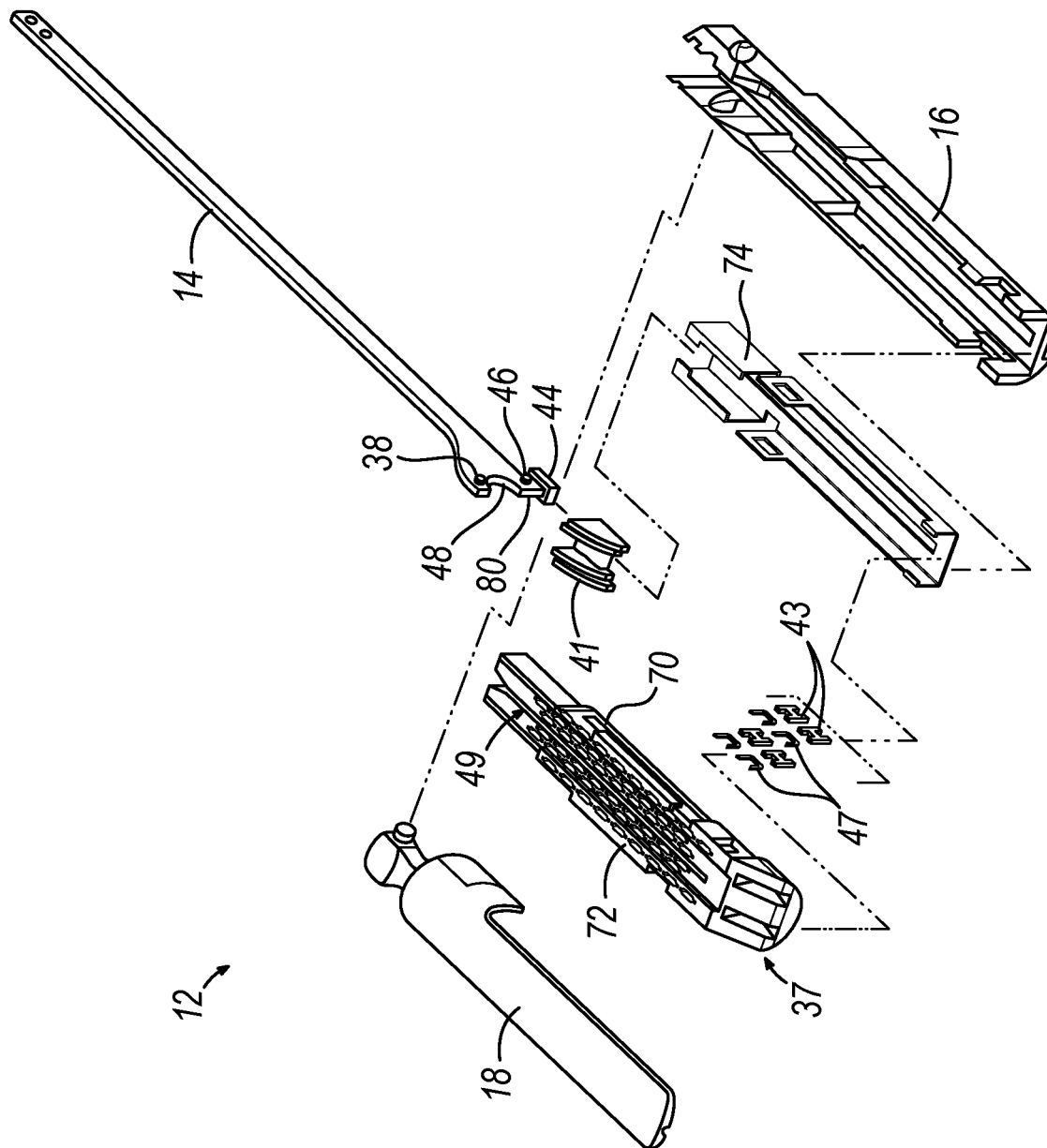
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), firing beam (14) is then advanced distally into engagement with anvil (18) by having upper pin (38) enter longitudinal anvil slot (42). A pusher block (80) (shown in FIG. 5) located at the distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B but are shown in FIG. 3. Anvil (18) is intentionally omitted from the view in FIG. 5.

Figure 7:
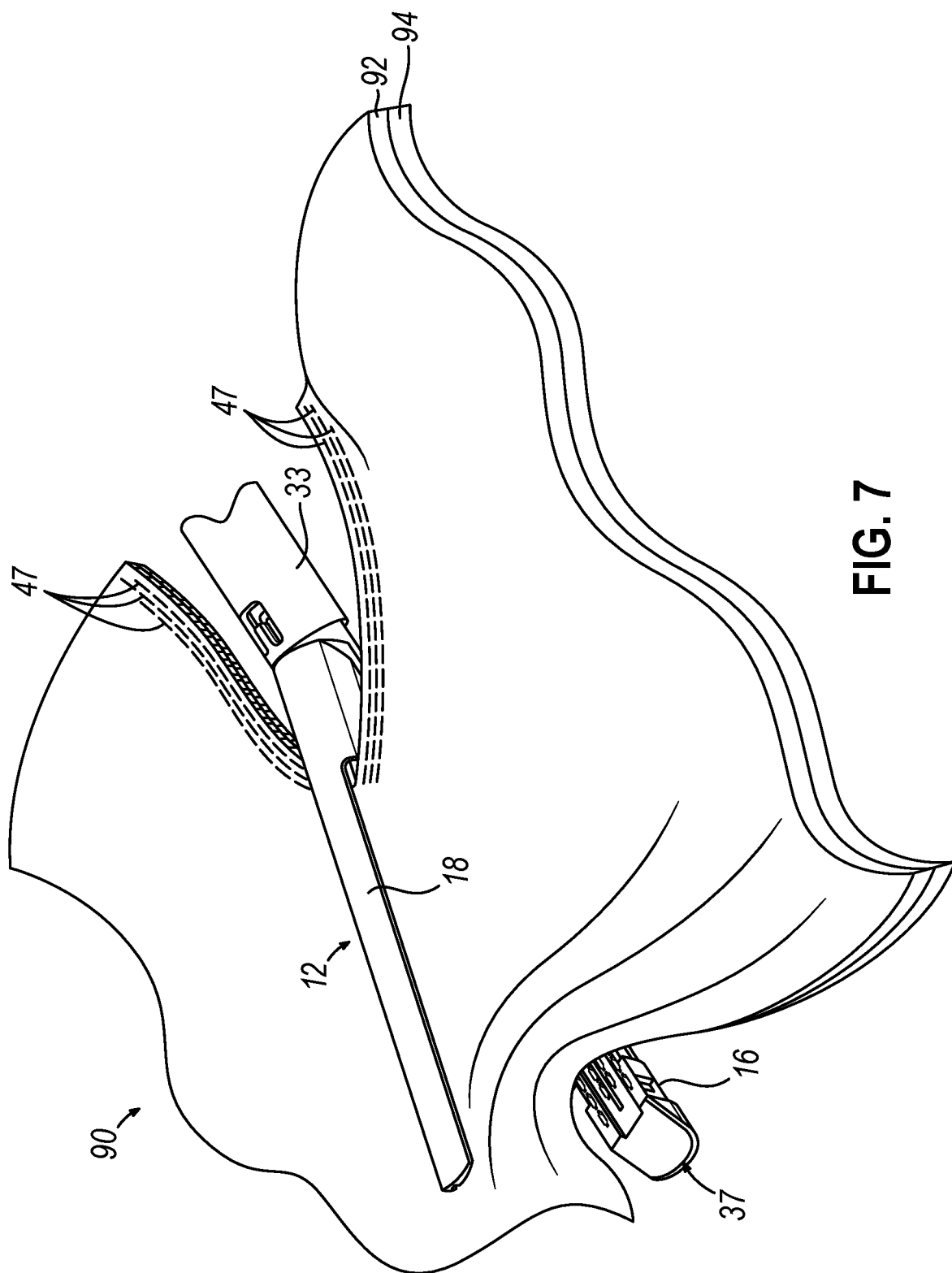
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through the tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly and Buttress Applier Cartridge

In some instances, it may be desirable to equip end effector (12) of surgical instrument (10) with an adjunct material, such as a buttress, to reinforce the mechanical fastening of tissue provided by staples (47). Such a buttress may prevent the applied staples (47) from pulling through the tissue and may otherwise reduce a risk of tissue tearing at or near the site of applied staples (47). In addition to or as an alternative to providing structural support and integrity to a line of staples (47), a buttress may provide various other kinds of effects such as spacing or gap-filling, administration of therapeutic agents, and/or other effects. In some instances, a buttress may be provided on upper deck (72) of staple cartridge (37). As described above, deck (72) houses staples (47), which are driven by staple driver (43). In some other instances, a buttress may be provided on the surface of anvil (18) that faces staple cartridge (37). It should also be understood that a first buttress may be provided on upper deck (72) of staple cartridge (37) while a second buttress is provided on anvil (18) of the same end effector (12).

Various examples of forms that a buttress may take will be described in greater detail below. Various ways in which a buttress may be secured to a staple cartridge (37) or an anvil (18) will also be described in greater detail below. Exemplary buttress assemblies, exemplary materials and techniques for applying buttress assemblies, and exemplary buttress applier cartridges may be configured in accordance with at least some of the teachings of U.S. Pat. No. 10,166,023, entitled "Method of Applying a Buttress to a Surgical Stapler End Effector," issued Jan. 1, 2019; and/or in U.S. Pat. No. 10,349,939, entitled "Method of Applying a Buttress to a Surgical Stapler," issued Jul. 16, 2019, the disclosures of which are incorporated by reference herein.

A. Exemplary Composition of Buttress Assembly

Figure 8:
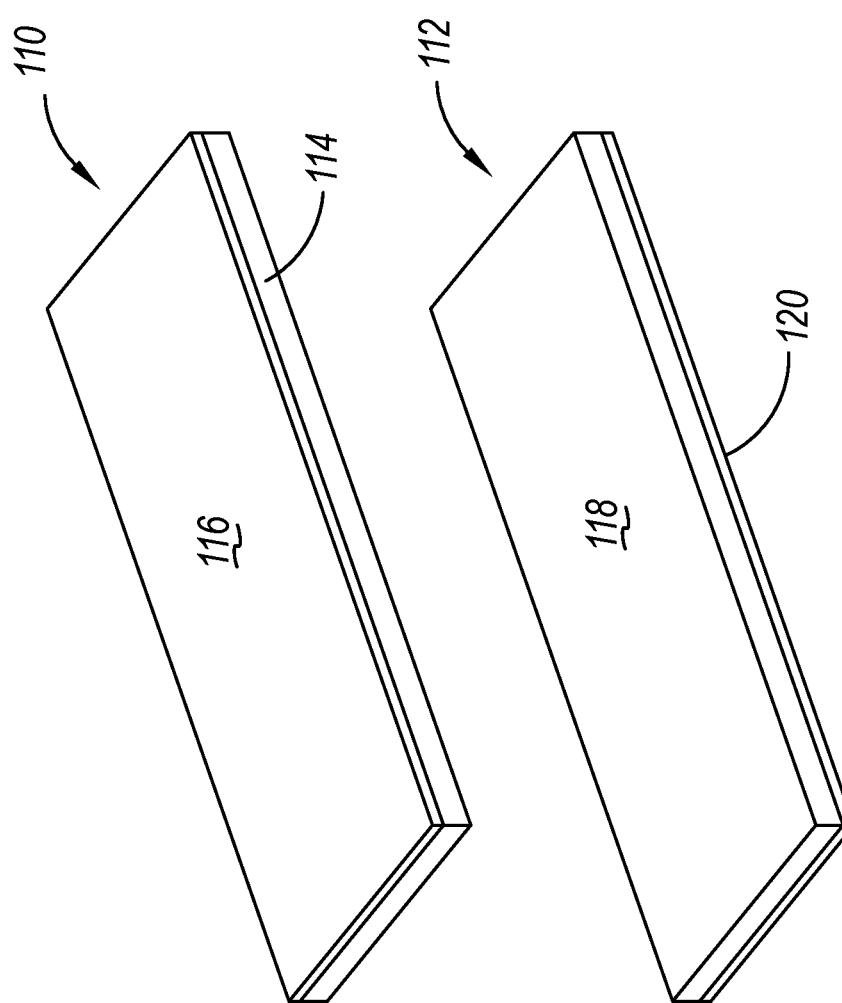
FIG. 8 depicts a perspective view of an exemplary pair of buttress assemblies, each of which may be applied to a jaw of the end effector of FIG. 3.

FIG. 8 shows an exemplary pair of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (47). By way of example only, each buttress body (114, 118) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to underside (124) of anvil (18). Similarly, adhesive layer (120) is provided on buttress body (118) to adhere buttress body (118) to upper deck (72) of staple cartridge (37). Such an adhesive material may provide proper positioning of buttress body (114, 118) before and during actuation of end effector (12); then allow buttress body (114, 118) to separate from end effector (12) after end effector (12) has been actuated, without causing damage to buttress body (114, 118) that is substantial enough to compromise the proper subsequent functioning of buttress body (114, 118).

B. Exemplary Stapling of Tissue with Buttress Assemblies

Figure 9:
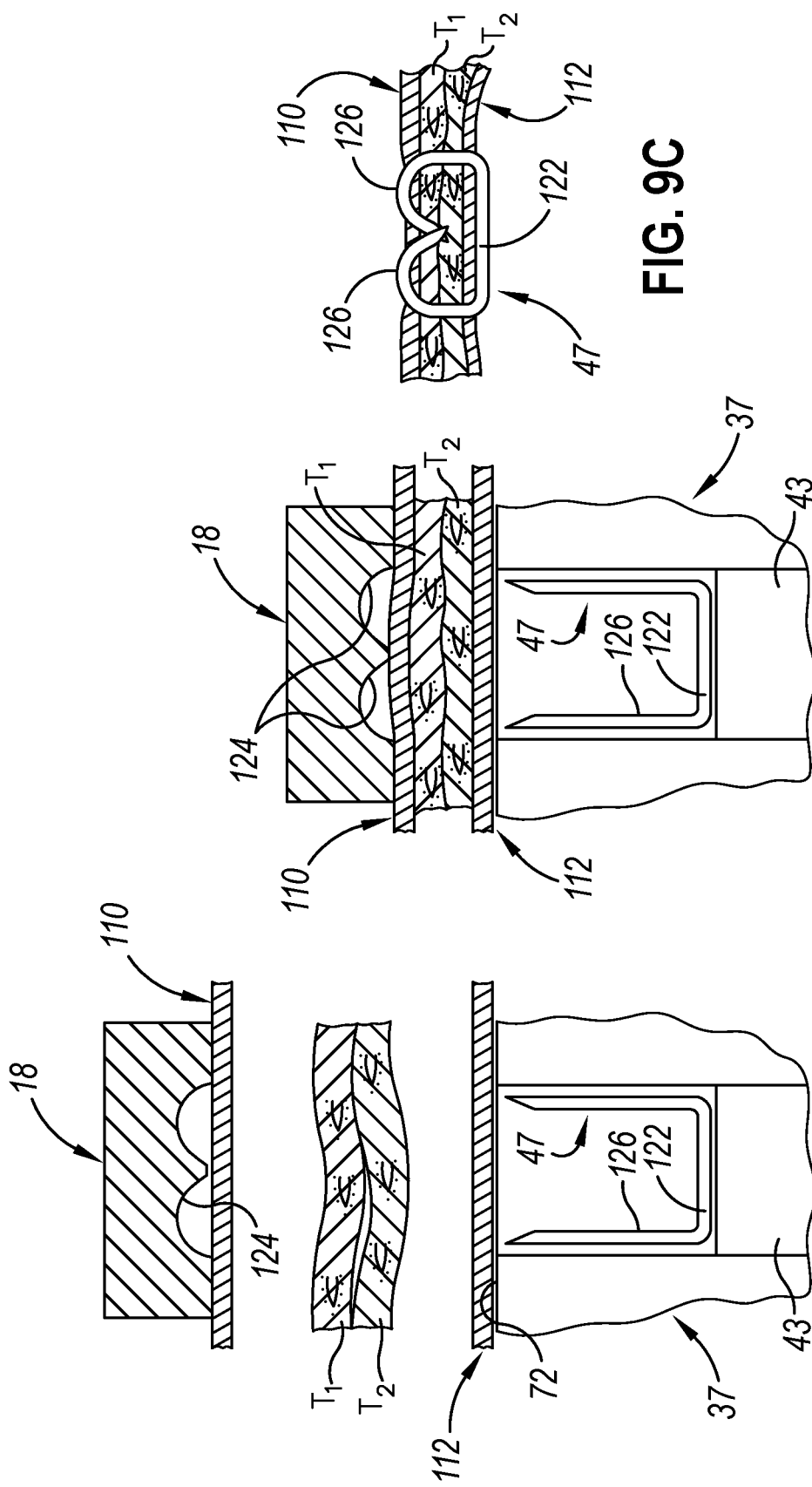
FIG. 9A depicts a cross-sectional end view of a portion of the end effector of FIG. 3 with the buttress assemblies of FIG. 8 applied to the upper and lower jaws of the end effector, showing the end effector jaws in an open state with tissue positioned between the upper and lower jaws.
FIG. 9B depicts a cross-sectional end view of the end effector and buttress assemblies of FIG. 9A, showing the end effector jaws in a closed state on the tissue.
FIG. 9C depicts a cross-sectional view of a formed staple and the buttress assemblies of FIG. 9A after having been secured to the tissue by the end effector of FIG. 3.

FIGS. 9A-9C show an exemplary sequence in which surgical stapler end effector (12), which has been loaded with buttress assemblies (110, 112), is actuated to drive staples (47) through two opposed layers of tissue ($T_1$, $T_2$), with buttress assemblies (110, 112) being secured to the same layers of tissue ($T_1$, $T_2$) by staples (47). In particular, FIG. 9A shows layers of tissue ($T_1$, $T_2$) positioned between anvil (18) and staple cartridge (37), with anvil (18) in the open position. Buttress assembly (110) is adhered to underside (124) of anvil (18) via adhesive layer (116); while buttress assembly (112) is adhered to upper deck (72) of staple cartridge (37) via adhesive layer (120). Layers of tissue ($T_1$, $T_2$) are thus interposed between buttress assemblies (110, 112). Next, closure trigger (26) is pivoted toward pistol grip (24) to drive closure tube (32) and closure ring (33) distally. This drives anvil (18) to the closed position as shown in FIG. 9B. At this stage, layers of tissue ($T_1$, $T_2$) are compressed between anvil (18) and staple cartridge (37), with buttress assemblies (110, 112) engaging opposite surfaces of tissue layers ($T_1$, $T_2$). End effector (12) is then actuated as described above, driving staple (47) through buttress assemblies (110, 112) and tissue ($T_1$, $T_2$). As shown in FIG. 13C, crown (122) of driven staple (47) captures and retains buttress assembly (112) against layer of tissue ($T_2$). Deformed legs (126) of staple (47) capture and retain buttress assembly (110) against layer of tissue ($T_1$).

Figure 10:
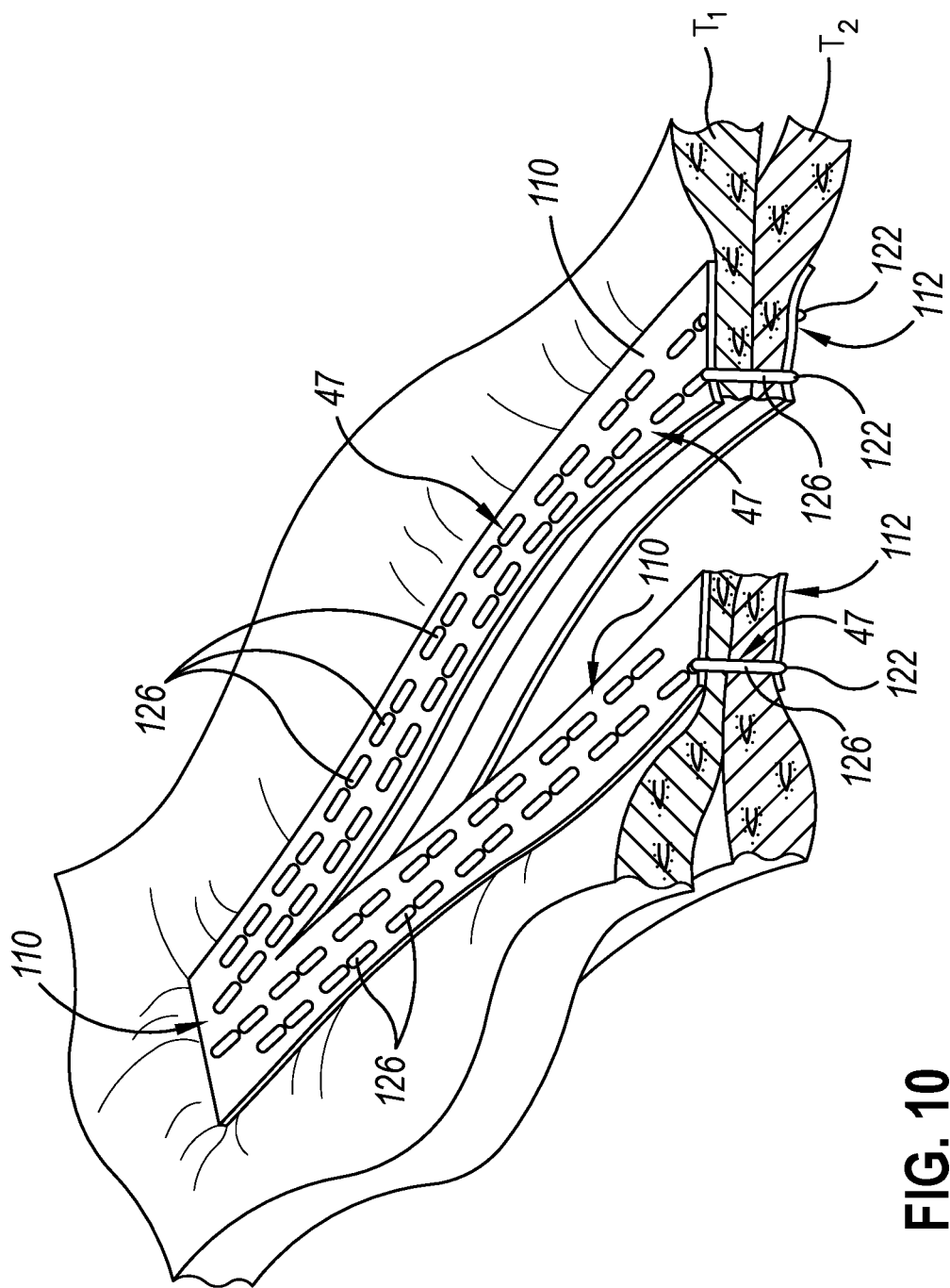
FIG. 10 depicts a perspective view of formed staples and the buttress assemblies of FIG. 9A after having been secured to the tissue by the end effector of FIG. 3.

A series of staples (47) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (12) is pulled away from tissue ($T_1$, $T_2$) after deploying staples (47) and buttress assemblies (110, 112), buttress assemblies (110, 112) disengage end effector such that buttress assemblies (110, 112) remain secured to tissue ($T_1$, $T_2$) with staples (47). Buttresses (110, 112) thus provides structural reinforcement to the lines of staples (47) formed in tissue ($T_1$, $T_2$). As can also be seen in FIG. 10, distally presented cutting edge (48) of firing beam (14) also cuts through a centerline of buttress tissue assemblies (110, 112), separating each buttress assembly (110, 112) into a corresponding pair of sections, such that each section remains secured to a respective severed region of tissue ($T_1$, $T_2$).

C. Exemplary Buttress Applier Cartridge With Active Retainer Arms

Figure 11:
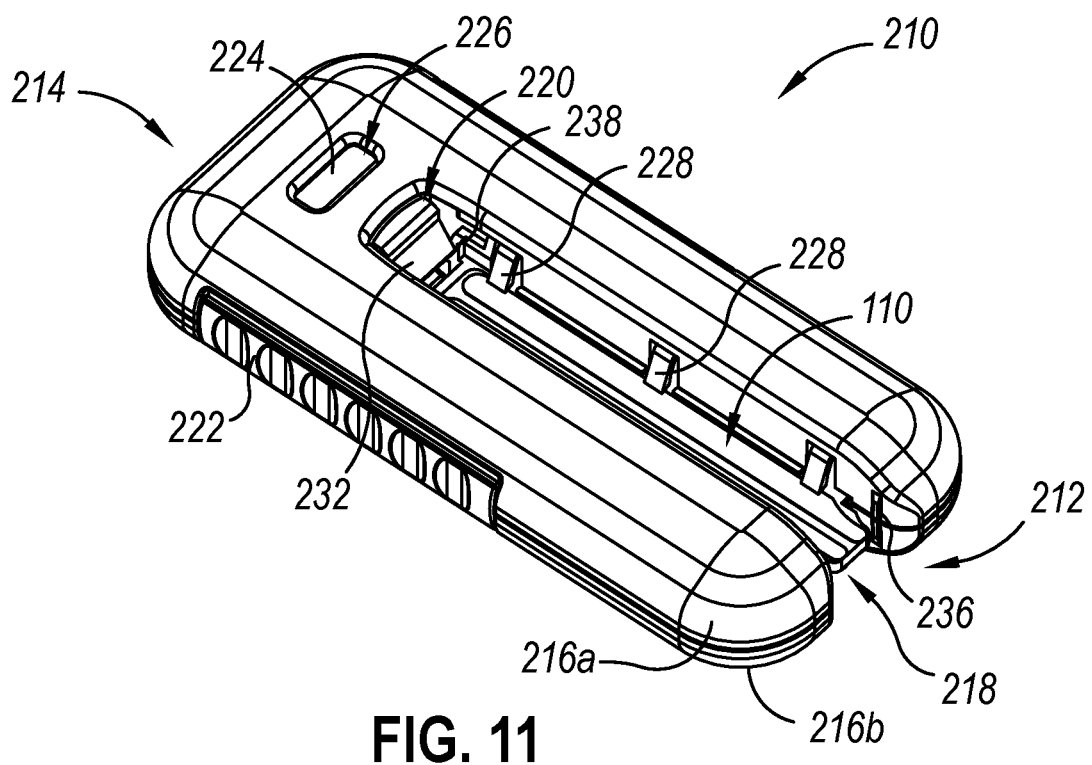
FIG. 11 depicts a perspective view of an exemplary buttress applier cartridge that may be used to carry and apply the buttress assemblies of FIG. 8.
Figure 12:
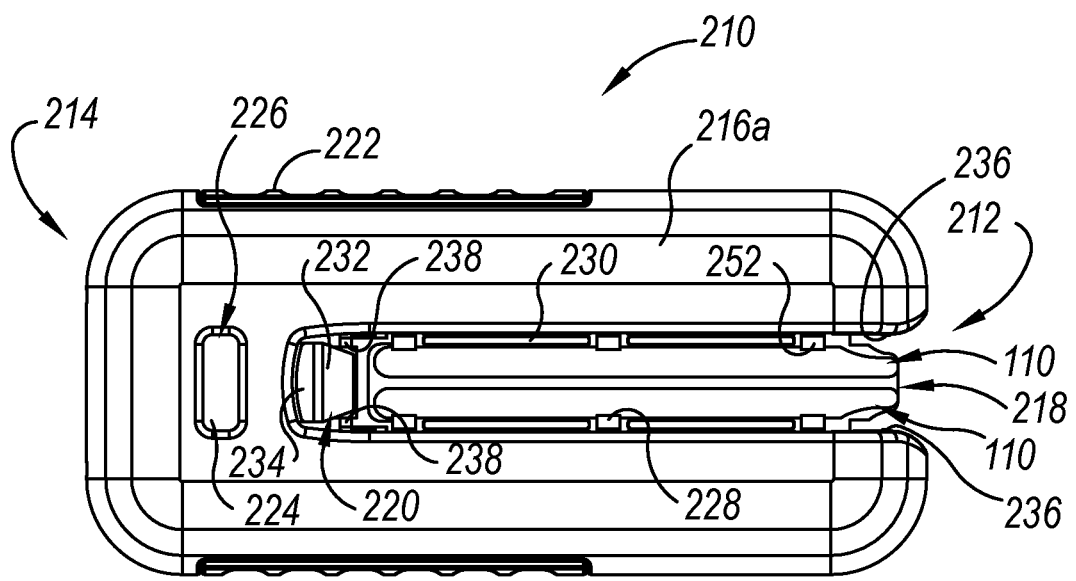
FIG. 12 depicts a top plan view of the buttress applier cartridge of FIG. 11.

Because end effector (12) of surgical instrument (10) may be actuated multiple times during a single surgical procedure, it may be desirable to enable an operator to repeatedly and easily load buttress assemblies (110, 112) onto end effector jaws (16, 18) during that single surgical procedure. FIGS. 11-13B show an exemplary buttress applier cartridge (210) (also referred to as a "buttress applicator") that may be used to support, protect, and apply adjunct material, such as buttress assemblies (110, 112), to end effector (12). As best seen in FIGS. 11-12, cartridge (210) of this example comprises an open end (212) and a closed end (214). Open end (212) is configured to receive end effector (12) as will be described in greater detail below. Cartridge (210) further includes a first housing (216a) and a second housing (216b), which each collectively generally define a "U" shape to present open end (212). A platform (218) and a sled retainer (220) are interposed between first and second housings (216a, 216b).

Platform (218) of the present example is configured to support a pair of buttress assemblies (110) on one side of platform (218) and another pair of buttress assemblies (112) on the other side of platform (218). Platform (218) is exposed in recesses that are formed between the prongs of the "U" configuration of first and second housings (216a, 216b). Each buttress assembly (110, 112) is provided in a respective pair of portions that are separated to avoid spanning across slots (42, 49) of anvil (18) and staple cartridge (37), respectively, though platform (218) may just as easily support wide versions of buttress assemblies (110, 112) that unitarily span across slots (42, 49) of anvil (18) and staple cartridge (37), respectively. More specifically, the outer edges of platform (218) include retention features (530) in the form of ridges that further engage first and second housings (216a, 216b) to prevent platform (218) from sliding relative to first and second housings (216a, 216b).

First and second housings (216a, 216b) include integral gripping features (222) and indicator plates (224) positioned to correspond with windows (226) formed in first and second housings (216a, 216b), such that indicator plates (224) are visible through windows (226) at different times. Arms (228) of the present example are configured to selectively secure buttress assemblies (110, 112) to platform (218). In the present example, arms (228) are resilient and are thus configured to resiliently bear against buttress assemblies (110, 112), thereby pinching buttress assemblies (110, 112) against platform (218). Buttress applier cartridge (210) includes a pair of tapered cam surfaces (232) and a respective pair of housing engagement features (234) positioned to engage corresponding surfaces of first and second housings (216a, 216b). First and second housings (216a, 216b) include proximal guide features (236) and distal guide features (238) configured to assist in providing proper alignment of end effector (40) with cartridge (210).

Figure 13A:
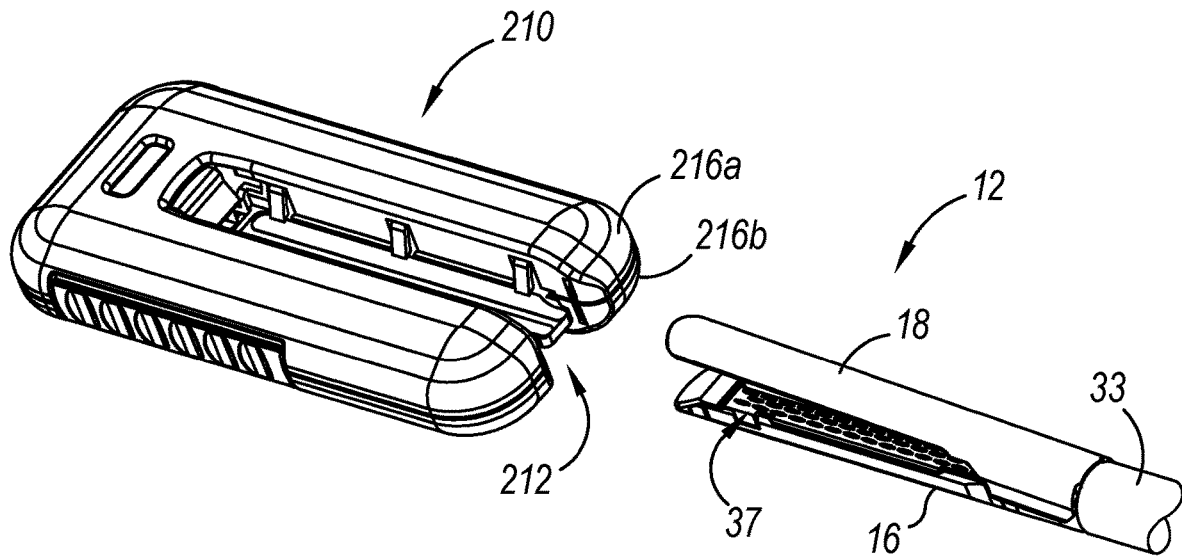
FIG. 13A depicts a perspective view of the end effector of FIG. 3 and the buttress applier cartridge of FIG. 11, showing the end effector and the buttress applier cartridge being aligned with one another.
Figure 13B:
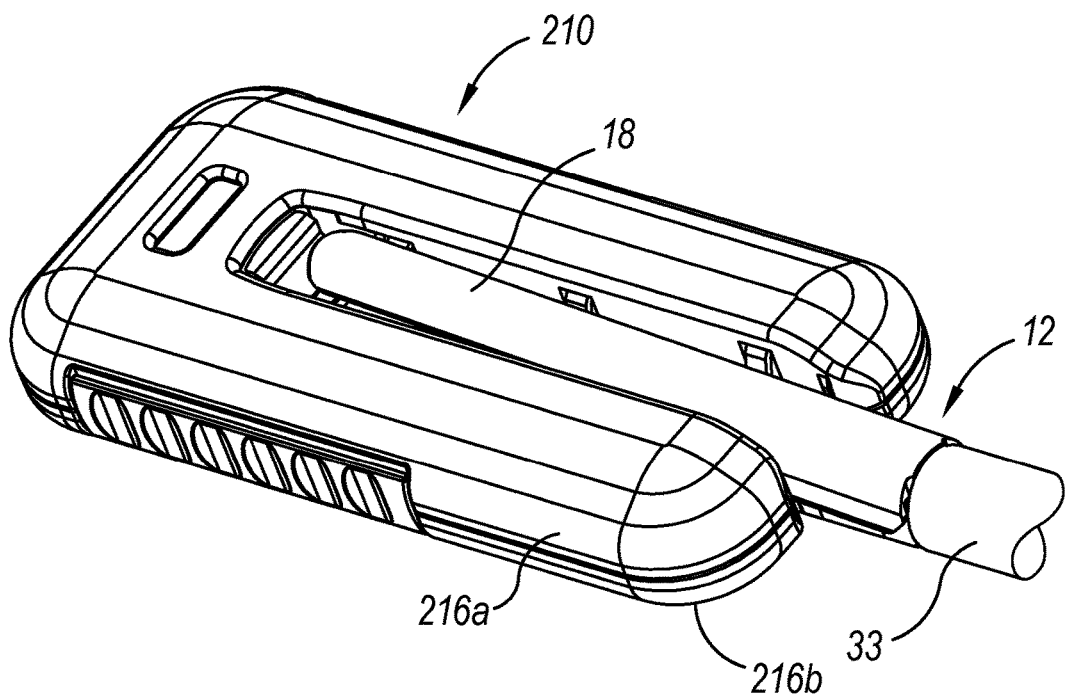
FIG. 13B depicts a perspective view of the end effector of FIG. 3 and the buttress applier cartridge of FIG. 11, with the end effectors jaws closed on a platform of the buttress applier cartridge.

FIG. 13A shows cartridge (210) in a configuration where retainer arms (228) are positioned to hold buttress assemblies (110, 112) against platform (218); while FIG. 13B shows cartridge (210) in a configuration where retainer arms (228) are positioned to release buttress assemblies (110, 112) from platform (218). While FIGS. 13A-13B only show buttress assembly (110) on platform (218), buttress assembly (112) would be retained on and released from platform (218) in an identical fashion. To use cartridge (210) to load end effector (12), the operator would first position cartridge (210) and end effector (12) such that end effector is aligned with open end (212) of cartridge (210) as shown in FIG. 13A. The operator would then advance end effector (12) distally, and/or advance cartridge (210) proximally, to position platform (218) and buttress assemblies (110, 112) between anvil (18) and staple cartridge (37) as shown in FIG. 13B. Closure trigger (26) of instrument (10) is then squeezed by the operator to close end effector jaws (16, 18) on platform (218), thereby adhesively attaching buttress assemblies (110, 112) to anvil (18) and staple cartridge (37), and simultaneously depressing cam surface (232). Depression of cam surface (232) actuates retainer arms (228) laterally outwardly to thereby release buttress assemblies (110, 112) from platform (218), such that end effector jaws (16, 18) may be disengaged from platform (218) while buttress assemblies (110, 112) remain adhered to anvil (18) and staple cartridge (37).

III. Exemplary Alternative Applicator Devices and Related Methods of Applying a Buttress to a Surgical Stapler End Effector In some instances, it may be desirable to provide an applicator device that is configured to apply a staple reinforcing adjunct element to one or both jaws of a surgical stapler end effector without closing the jaws via actuation of the stapler's end effector closure system, such as via actuation of closure trigger (26) of surgical stapler (10). The exemplary applicator devices described below provide such functionality, such that each applicator device is configured to be manipulated relative to an end effector to apply an adjunct element to one or both jaws without requiring actuated closure of the jaws like that shown in FIGS. 13A-13B described above. Additionally, the exemplary applicator devices described below may be operable to apply a minimum pressure to appropriately seat the adjunct material on the desired jaw (e.g., lower jaw (16) or anvil (18)).

It will be appreciated that any of the exemplary applicator devices described below may be configured to apply an adjunct element in the form of a buttress, such as buttresses (110, 112) described above, or a tissue thickness compensator, for example of the type disclosed in U.S. Pat. Pub. No. 2012/0080336, entitled "Staple Cartridge Comprising Staples Positioned Within A Compressible Portion Thereof," published Apr. 5, 2012 and now abandoned, the disclosure of which is incorporated by reference herein. Additionally, application of a staple reinforcement element to an end effector jaw may be achieved with adhesive features as described above and/or with mechanical coupling features, for example of the type disclosed in U.S. Pat. No. 7,665,646, entitled "Interlocking Buttress Material Retention System," issued Feb. 23, 2010, the disclosure of which is incorporated by reference herein. Furthermore, any of the exemplary applicator devices described below may be suitably constructed for a single use or for multiple uses.

Figure 14:
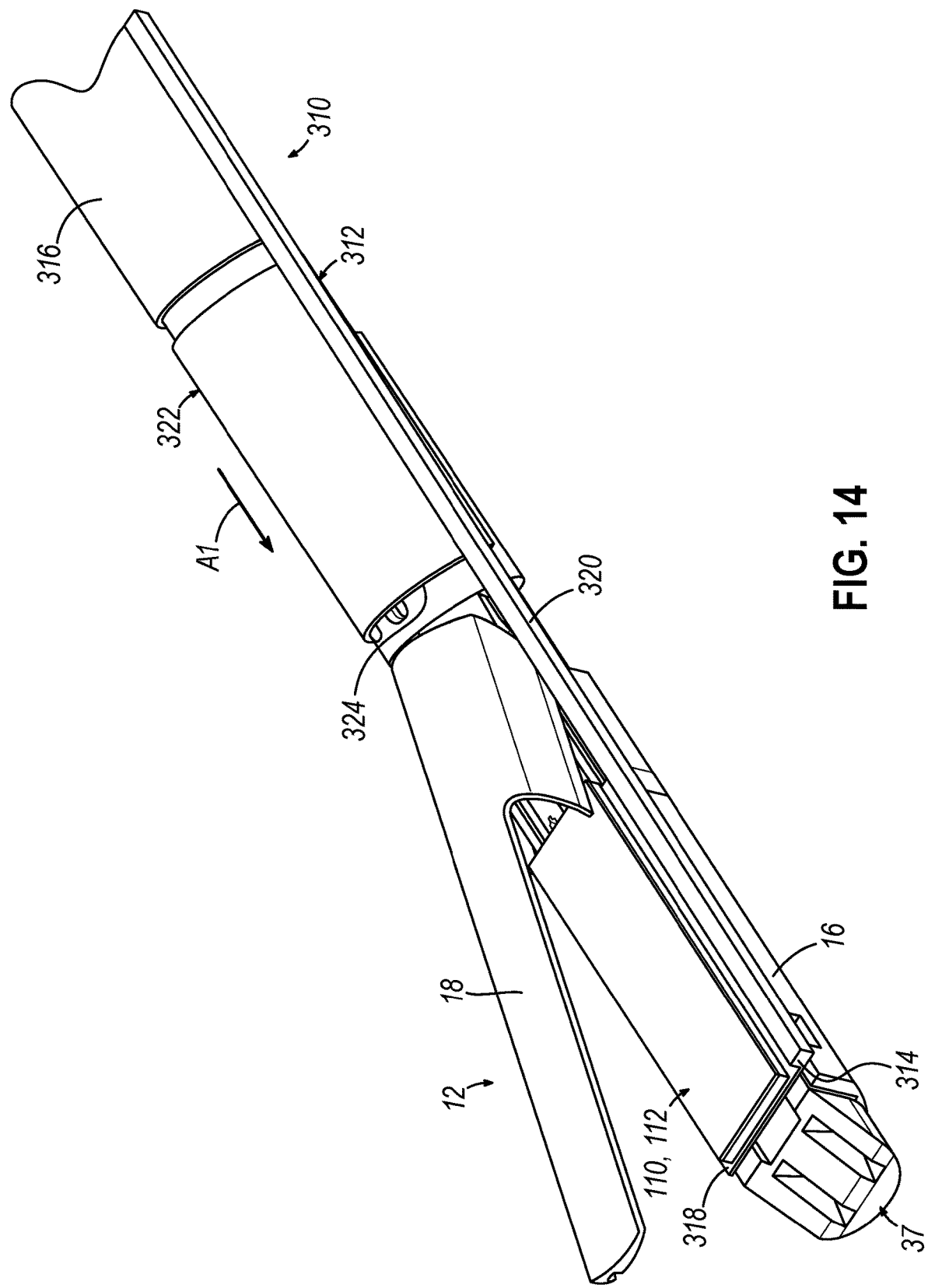
FIG. 14 depicts a perspective view of the end effector of FIG. 3 and another exemplary buttress applicator that may be used to carry and apply the buttress assemblies of FIG. 8, showing the buttress applicator positioned over the end effector with a translatable sleeve of the buttress applicator in a retracted position.

A. Exemplary Buttress Applicator With Translatable Sleeve for Back-Driving End Effector Jaws FIGS. 14-15B show an exemplary buttress applicator (310) configured to force the jaws of an end effector to close onto a portion of buttress applicator (310) supporting one or more buttress assemblies (110, 112), or otherwise "back-drive" the jaws of the end effector for applying buttress assemblies (110, 112) thereon. Buttress applicator (310) is similar to buttress applicator (210) described above except as otherwise described below.

Buttress applicator (310) of this example comprises a frame (312) extending between a proximal end (not shown) and a distal end (314). Frame (312) includes a handle (316) positioned at or near the proximal end of frame (312), a compression pad or platform (318) positioned at or near the distal end (314) of frame (312), and an elongate rail (320) extending longitudinally therebetween. In the example shown, rail (320) extends along lateral sides of handle (316) and platform (318) such that rail (320) is capable of being positioned alongside end effector (12). While a single rail (320) is shown, frame (312) may include a pair of opposing rails (320), for example. Buttress applicator (310) further comprises a movable member in the form of a translatable sleeve (322) coupled to frame (312) and configured to translate longitudinally relative to platform (318) along rail (320) as indicated by first arrow (A1) in FIG. 14, and to selectively receive end effector (12) as will be described in greater detail below.

Platform (318) of the present example is configured to support at least one buttress assembly (110, 112) on at least one side of platform (318). In the example shown, platform (318) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively. While platform (318) is shown supporting buttress assembly (110, 112) on only a single side of platform (318), platform (318) may just as easily support buttress assemblies (110, 112) on both sides of platform (318).

Translatable sleeve (322) has a generally C-shaped cross section and includes a generally C-shaped inner closure surface (324) configured to selectively mechanically engage an outer external surface of at least one of end effector jaws (16, 18) to thereby transition end effector (12) from an open state toward a closed state when platform (318) is positioned between jaws (16, 18). In this regard, sleeve (322) may be sized and configured relative to end effector (12) such that closure surface (324) is capable of at least partially circumferentially surrounding or encircling end effector (12) and to be in contact or near-contact with an outer external surface of at least one of jaws (16, 18) for constricting end effector (12) in the closed state. For example, closure surface (324) may define a cross dimension (e.g., diameter) substantially equal to or slightly greater than a distance between outer external surfaces of jaws (16, 18) when end effector (12) is in the closed state. Sleeve (322) and/or rail (320) may also be sized and configured to assist in providing proper alignment of end effector (12) with buttress applicator (310), such as by allowing rail (320) to abut a lateral side of end effector (12) when buttress applicator (310) is positioned over end effector (12) with platform (318) properly positioned between jaws (16, 18).

FIG. 15A shows end effector (12) in the open state and buttress applicator (310) in a configuration where sleeve (322) is in a retracted position relative to end effector (12) such that closure surface (324) is mechanically disengaged from the outer external surface of upper jaw (18); while FIG. 15B shows buttress applicator (310) in a configuration where sleeve (322) is in an extended position relative to end effector (12) such that closure surface (324) mechanically engages the outer external surface of upper jaw (18) to thereby transition end effector (12) from the open state toward the closed state. To use buttress applicator (310) to load end effector (12), the operator would first position buttress applicator (310) and end effector (12) such that platform (318) and buttress assembly (110, 112) are positioned between anvil (18) and staple cartridge (37) and such that end effector (12) is aligned with sleeve (322) with sleeve (322) retracted proximally from jaws (16, 18) as shown in FIG. 15A. The operator would then advance sleeve (322) distally relative to end effector (12) to mechanically engage closure surface (324) with the outer external surface of anvil (18) as indicated by second arrow (A2) in FIG. 15B. End effector jaws (16, 18) may be back-driven closed on platform (318) by such mechanical engagement (e.g., while closure trigger (26) of instrument (10) remains unactuated), thereby adhesively attaching buttress assembly (110, 112) to anvil (18) (e.g., to the stapling surface thereof). Buttress assembly (110, 112) may be released from platform (318), such that end effector jaws (16, 18) may be disengaged from platform (318) while buttress assembly (110, 112) remains adhered to anvil (18). In one example, sleeve (322) may be sequentially advanced and retracted in a back-and-forth or "pumping" manner to incrementally transition end effector (12) toward the closed state.

While buttress applicator (310) is shown applying buttress assembly (110, 112) to anvil (18), buttress applicator (310) may additionally or alternatively apply buttress assembly (110, 112) to lower jaw (16), such as to stapler cartridge (37) (e.g., to the stapling surface thereof).

Figure 16:
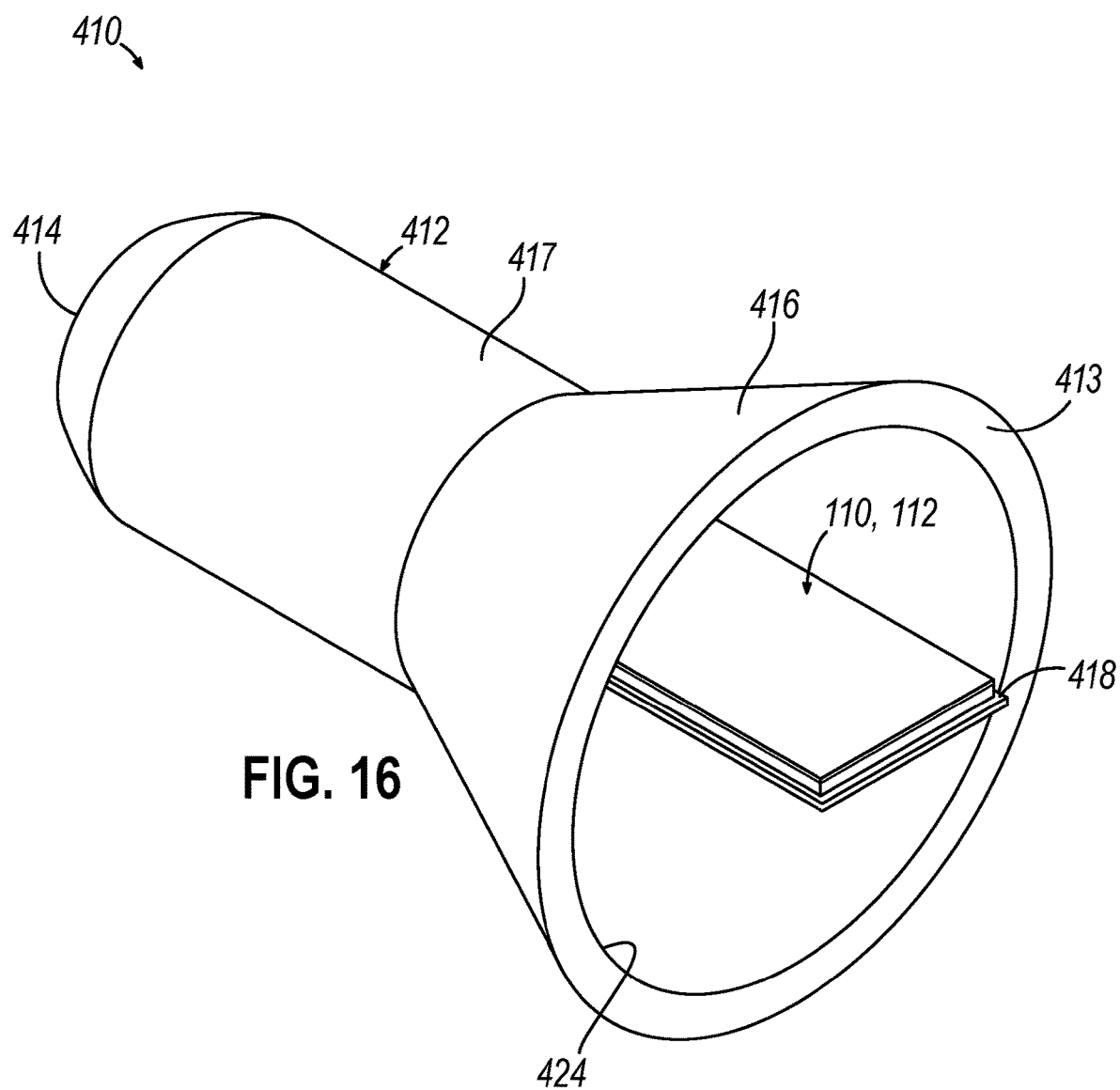
FIG. 16 depicts a perspective view of another exemplary buttress applicator that may be used to carry and apply the buttress assemblies of FIG. 8.

B. Exemplary Buttress Applicator With Tapered Camming Surface for Back-Driving End Effector Jaws FIGS. 16-17B show another exemplary buttress applicator (410) configured to force the jaws of an end effector to close onto a portion of buttress applicator (410) supporting one or more buttress assemblies (110, 112), or otherwise "back-drive" the jaws of the end effector for applying buttress assemblies (110, 112) thereon. Buttress applicator (410) is similar to buttress applicators (210, 310) described above except as otherwise described below.

Buttress applicator (410) of this example comprises a housing (412) extending between an open proximal end (413) and a closed distal end (414). Housing (412) includes a generally frustoconical proximal portion (416) and a generally cylindrical distal portion (417) such that housing (412) is generally funnel-shaped. A compression pad or platform (418) extends proximally from closed distal end (414) within proximal and distal portions (416, 417) of housing (412) and is fixed against movement relative thereto. Housing (412) is configured to selectively receive end effector (12) as will be described in greater detail below.

Platform (418) of the present example is configured to support at least one buttress assembly (110, 112) on at least one side of platform (418). In the example shown, platform (418) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively. While platform (418) is shown supporting buttress assembly (110, 112) on only a single side of platform (418), platform (418) may just as easily support buttress assemblies (110, 112) on both sides of platform (418).

Proximal and distal portions (416, 417) of housing (412) include tapered and untapered inner closure surfaces (424, 426), respectively, configured to selectively mechanically engage an outer external surface of at least one of end effector jaws (16, 18) to thereby transition end effector (12) from an open state toward a closed state when platform (418) is positioned between jaws (16, 18). In this regard, proximal and distal portions (416, 417) may be sized and configured relative to end effector (12) such that closure surfaces (424, 426) are capable of at least partially circumferentially surrounding or encircling end effector (12) and to be in contact or near-contact with an outer external surface of at least one of jaws (16, 18) for constricting end effector (12) in the closed state. For example, untapered closure surface (426) may define a minor cross dimension (e.g., diameter) substantially equal to or slightly greater than a distance between outer external surfaces of jaws (16, 18) when end effector (12) is in the closed state; while tapered closure surface (424) may define a major cross dimension (e.g., diameter) substantially equal to or greater than a distance between outer external surfaces of jaws (16, 18) when end effector (12) is in the closed state, and may taper radially inwardly in a distal direction toward untapered closure surface (426). It will be appreciated that tapered closure surface (424) may alternatively be curved radially inwardly in a distal direction toward untapered closure surface (426). Proximal and/or distal portions (416, 417) may also be sized and configured to assist in providing proper alignment of end effector (12) with buttress applicator (410), such as by abutting one or more lateral sides of end effector (12) when buttress applicator (410) is positioned over end effector (12) with platform (418) properly positioned between jaws (16, 18).

Figure 17A:
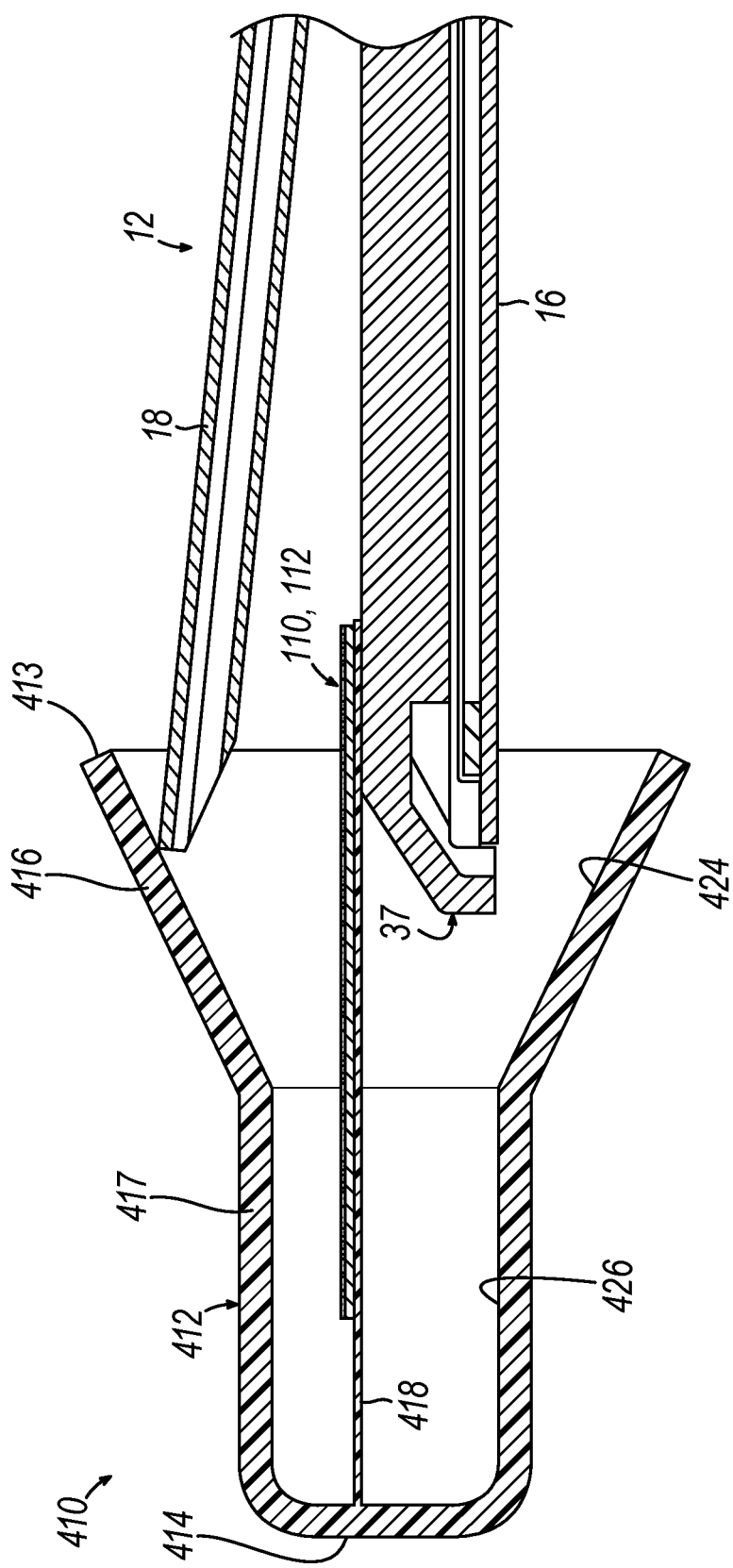
FIG. 17A depicts a side cross-sectional view of the buttress applicator of FIG. 16 and the end effector of FIG. 3, showing the applicator axially aligned with the end effector.
Figure 17B:
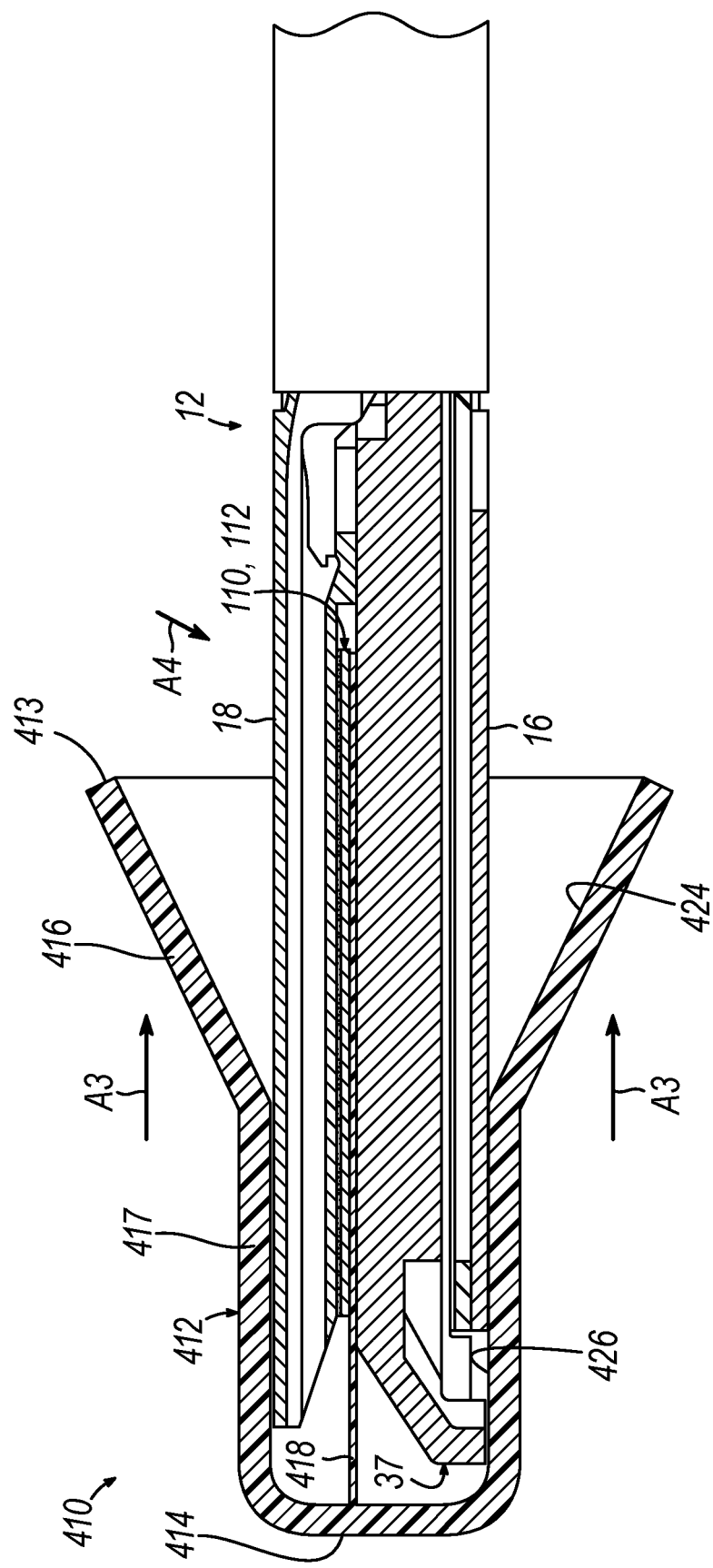
FIG. 17B depicts a side cross-sectional view of the buttress applicator of FIG. 16 positioned over the end effector of FIG. 3, showing the buttress applicator proximally advanced over the end effector for transitioning the end effector toward the closed state.

FIG. 17A shows buttress applicator (410) positioned relative to end effector (12) such that tapered closure surface (424) mechanically engages the outer external surface of upper jaw (18) to thereby transition end effector (12) from the open state toward the closed state; while FIG. 17B shows buttress applicator (410) positioned relative to end effector (12) such that untapered closure surface (326) mechanically engages the outer external surfaces of both jaws (16, 18) to thereby maintain end effector (12) in the closed state. To use buttress applicator (410) to load end effector (12), the operator would first position buttress applicator (410) and end effector (12) such that platform (418) and buttress assembly (110, 112) are positioned between anvil (18) and staple cartridge (37) and such that end effector (12) is received by proximal portion (416) of housing (412) as shown in FIG. 17A. The operator would then advance housing (412) proximally relative to end effector (12) to mechanically engage tapered closure surface (424) with the outer external surface of anvil (18) as indicated by third arrows (A3) in FIG. 17A such that anvil (18) is cammed radially inwardly as indicated by fourth arrow (A4) in FIG. 17A until untapered closure surface (426) mechanically engages the outer external surfaces of both jaws (16, 18) as shown in FIG. 17B. End effector jaws (16, 18) may be back-driven closed on platform (418) by such mechanical engagement (e.g., while closure trigger (26) of instrument (10) remains unactuated), thereby adhesively attaching buttress assembly (110, 112) to anvil (18) (e.g., to the stapling surface thereof). Buttress assembly (110, 112) may be released from platform (418), such that end effector jaws (16, 18) may be disengaged from platform (418) while buttress assembly (110, 112) remains adhered to anvil (18), such as by retracting housing (412) distally relative to end effector (12).

While buttress applicator (410) is shown applying buttress assembly (110, 112) to anvil (18), buttress applicator (410) may additionally or alternatively apply buttress assembly (110, 112) to lower jaw (16), such as to stapler cartridge (37) (e.g., to the stapling surface thereof).

In one example, platform (418) may be omitted and housing (412) may be configured to selectively receive another buttress applicator or applier cartridge, such as cartridge (210), in place of platform (418). In this manner, buttress applicator (410) may be reusable by selectively inserting loaded cartridges (210) into housing (412) and removing spent cartridges (210) from housing (412).

Figure 18:
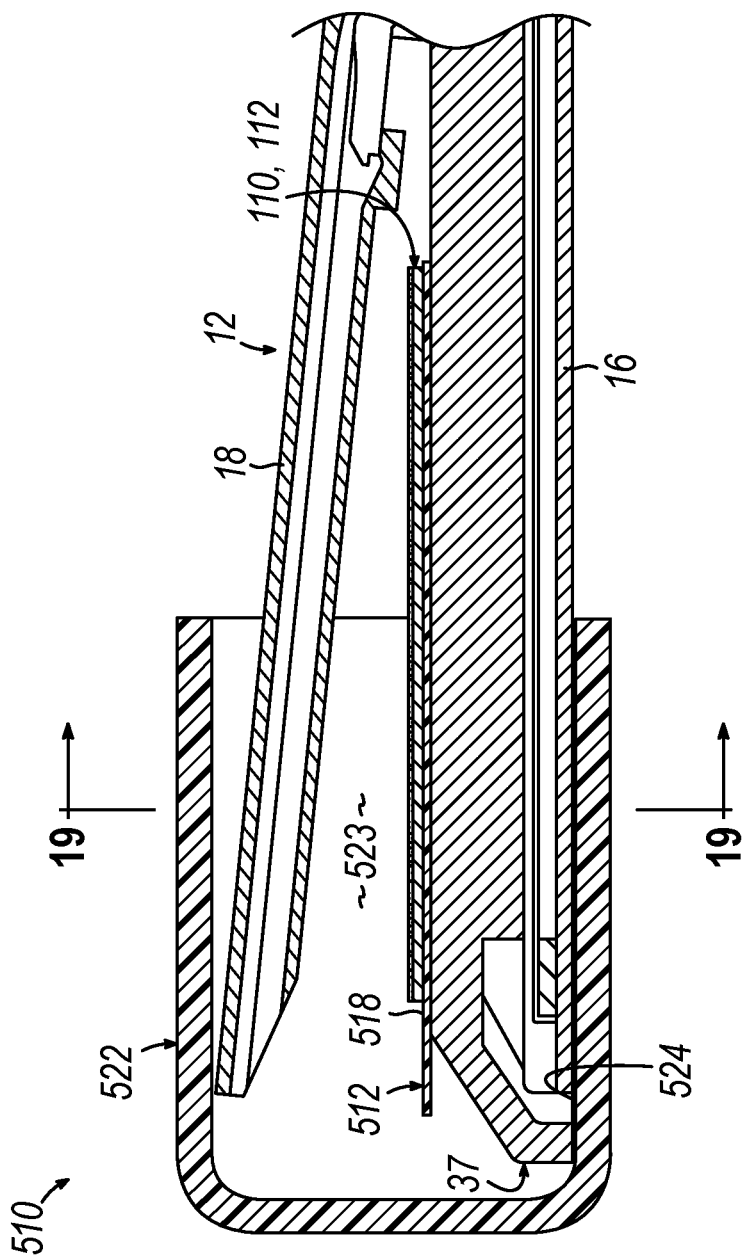
FIG. 18 depicts a side cross-sectional view of another exemplary buttress applicator that may be used to carry and apply the buttress assemblies of FIG. 8 positioned over the end effector of FIG. 3, showing a rotatable sleeve of the buttress applicator in a first angular (e.g., "unclocked") position.

C. Exemplary Buttress Applicator With Twistable Sleeve for Back-Driving End Effector Jaws FIGS. 18-19B show another exemplary buttress applicator (510) configured to force the jaws of an end effector to close onto a portion of buttress applicator (510) supporting one or more buttress assemblies (110, 112), or otherwise "back-drive" the jaws of the end effector for applying buttress assemblies (110, 112) thereon. Buttress applicator (510) is similar to buttress applicators (210, 310, 410) described above except as otherwise described below.

Buttress applicator (510) of this example comprises a frame (512) including a compression pad or platform (518). Buttress applicator (510) further comprises a movable member in the form of a rotatable sleeve (522) coupled to frame (512) and configured to rotate relative to platform (518) about a rotational axis (RA) parallel to a longitudinal axis of platform (518), and to selectively receive end effector (12) as will be described in greater detail below.

Platform (518) of the present example is configured to support at least one buttress assembly (110, 112) on at least one side of platform (518). In the example shown, platform (518) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively. While platform (518) is shown supporting buttress assembly (110, 112) on only a single side of platform (518), platform (518) may just as easily support buttress assemblies (110, 112) on both sides of platform (518).

Rotatable sleeve (522) includes a bore (523) having a generally oval or elliptical cross section defining a generally oval or elliptical inner closure surface (524) configured to selectively mechanically engage an outer external surface of at least one of end effector jaws (16, 18) to thereby transition end effector (12) from an open state toward a closed state when platform (518) is positioned between jaws (16, 18). In this regard, sleeve (522) may be sized and configured relative to end effector (12) such that closure surface (524) is capable of at least partially circumferentially surrounding or encircling end effector (12) and to be in contact or near-contact with an outer external surface of at least one of jaws (16, 18) for constricting end effector (12) in the closed state. For example, closure surface (524) may define a minor cross dimension (e.g., diameter) substantially equal to or slightly greater than a distance between outer external surfaces of jaws (16, 18) when end effector (12) is in the closed state, and may further define a major cross dimension (e.g., diameter) substantially equal to or greater than a distance between outer external surfaces of jaws (16, 18) when end effector (12) is in the closed state. Sleeve (522) may also be sized and configured to assist in providing proper alignment of end effector (12) with buttress applicator (510), such as by abutting one or more lateral sides of end effector (12) when buttress applicator (510) is positioned over end effector (12) with platform (518) properly positioned between jaws (16, 18).

Figure 19A:
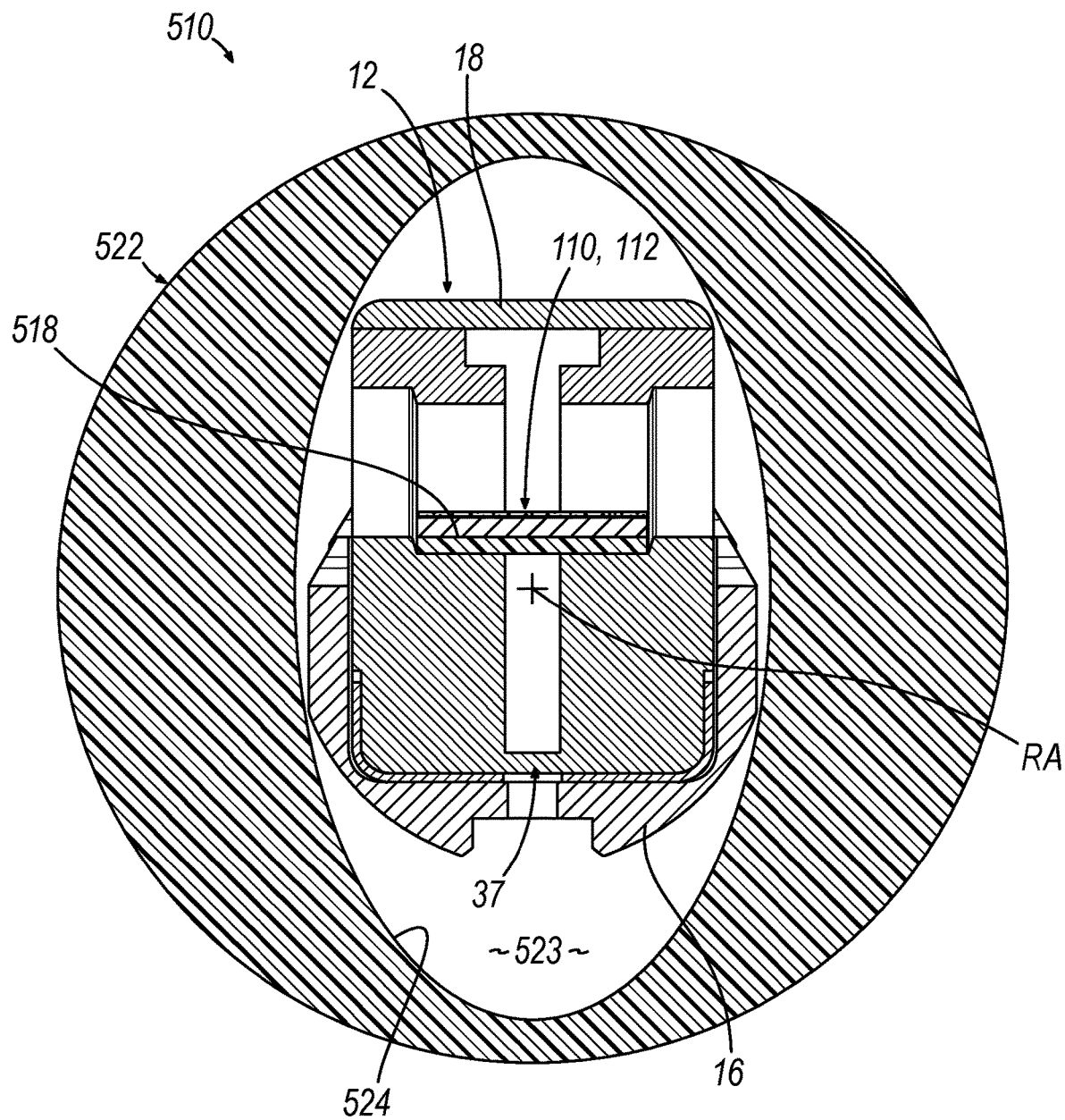
FIG. 19A depicts an end cross-sectional view of the buttress applicator of FIG. 18 positioned over the end effector of FIG. 3, taken along section line 19-19 in FIG. 18, showing the rotatable sleeve of the buttress applicator in the first angular position.
Figure 19B:
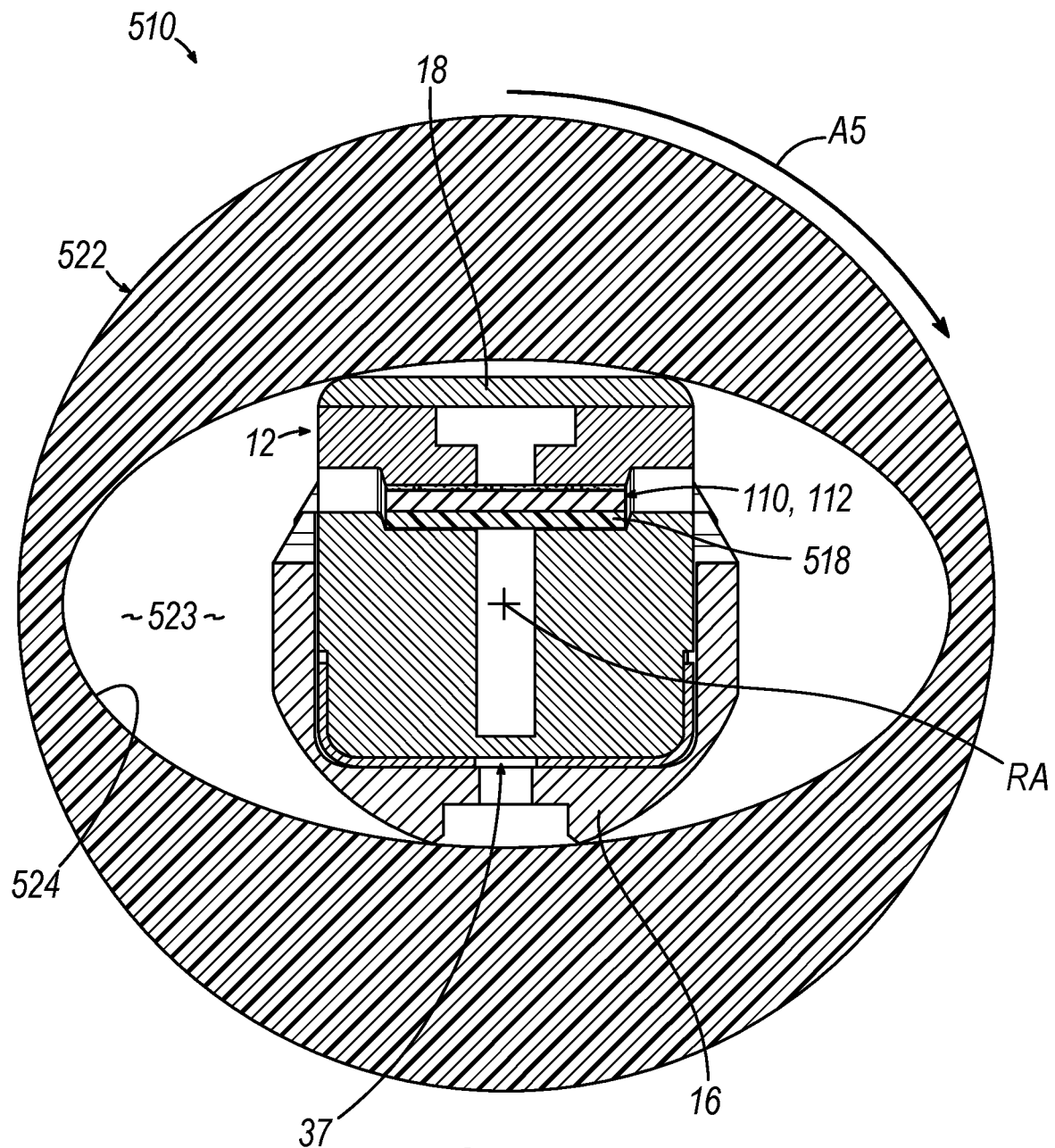
FIG. 19B depicts an end cross-sectional view of the buttress applicator of FIG. 18 positioned over the end effector of FIG. 3, taken along section line 19-19 in FIG. 18, showing the rotatable sleeve of the buttress applicator in a second angular (e.g., "clocked") position for transitioning the end effector toward the closed state.

FIG. 19A shows end effector (12) in the open state and buttress applicator (510) in a configuration where sleeve (522) is in a first angular (e.g., "unclocked") position relative to end effector (12) such that closure surface (524) is mechanically disengaged from the outer external surfaces of jaws (16, 18); while FIG. 19B shows buttress applicator (510) in a configuration where sleeve (522) is in a second angular (e.g., "clocked") position relative to end effector (12) such that closure surface (524) mechanically engages the outer external surfaces of jaws (16, 18) to thereby transition end effector (12) from the open state toward the closed state. To use buttress applicator (510) to load end effector (12), the operator would first position buttress applicator (510) and end effector (12) such that platform (518) and buttress assembly (110, 112) are positioned between anvil (18) and staple cartridge (37) and such that end effector (12) is received by sleeve (522) with sleeve (522) oriented about the rotational axis (RA) relative to end effector (12) in the first angular position as shown in FIG. 19A. The operator would then rotate sleeve (522) relative to end effector (12) about the rotational axis (RA) toward the second angular position to mechanically engage closure surface (524) with the outer external surfaces of both jaws (16, 18) as indicated by fifth arrow (A5) in FIG. 19B until the narrow or minor cross-dimension portion of closure surface (524) mechanically engages the outer external surfaces of both jaws (16, 18). End effector jaws (16, 18) may be back-driven closed on platform (518) by such mechanical engagement (e.g., while closure trigger (26) of instrument (10) remains unactuated), thereby adhesively attaching buttress assembly (110, 112) to anvil (18) (e.g., to the stapling surface thereof). Buttress assembly (110, 112) may be released from platform (518), such that end effector jaws (16, 18) may be disengaged from platform (518) while buttress assembly (110, 112) remains adhered to anvil (18), such as by rotating sleeve (522) relative to end effector (12) about the rotational axis (RA) to the first angular position.

While buttress applicator (510) is shown applying buttress assembly (110, 112) to anvil (18), buttress applicator (510) may additionally or alternatively apply buttress assembly (110, 112) to lower jaw (16), such as to stapler cartridge (37) (e.g., to the stapling surface thereof).

Figure 20:
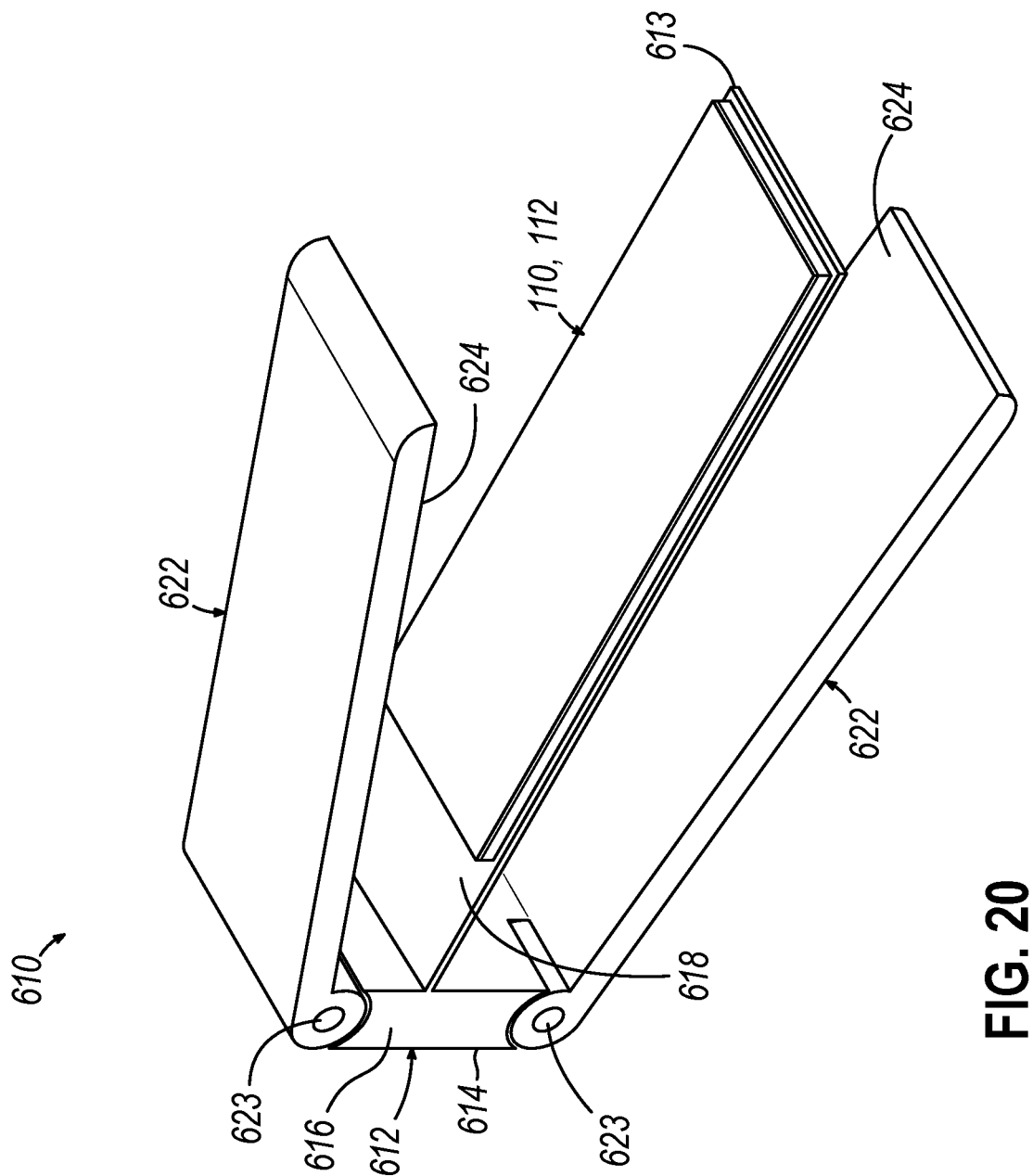
FIG. 20 depicts a perspective view of another exemplary buttress applicator that may be used to carry and apply the buttress assemblies of FIG. 8.

D. Exemplary Buttress Applicator With Hinged Lever Arms for Back-Driving End Effector Jaws FIGS. 20-21B show another exemplary buttress applicator (610) configured to force the jaws of an end effector to close onto a portion of buttress applicator (610) supporting one or more buttress assemblies (110, 112), or otherwise "back-drive" the jaws of the end effector for applying buttress assemblies (110, 112) thereon. Buttress applicator (610) is similar to buttress applicators (210, 310, 410, 510) described above except as otherwise described below.

Buttress applicator (610) of this example comprises a frame (612) extending between a proximal end (613) and a distal end (614). Frame (612) includes a dual hinge knuckle (616) positioned at or near distal end (614) of frame (612) and a compression pad or platform (618) extending proximally from knuckle (616) to proximal end (613). Buttress applicator (610) further comprises a pair of movable members in the form of opposing pivotable lever arms (622) coupled to knuckle (616) via respective hinge pins (623) and configured to pivot relative to platform (618) about respective lateral pivot axes (PA) extending in a direction perpendicular to a longitudinal axis of platform (618), and to selectively receive end effector (12) as will be described in greater detail below.

Platform (618) of the present example is configured to support at least one buttress assembly (110, 112) on at least one side of platform (618). In the example shown, platform (618) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively. While platform (618) is shown supporting buttress assembly (110, 112) on only a single side of platform (618), platform (618) may just as easily support buttress assemblies (110, 112) on both sides of platform (618).

Lever arms (622) are each generally flat and include respective generally flat inner closure surfaces (624) configured to selectively mechanically engage respective outer external surfaces of end effector jaws (16, 18) to thereby transition end effector (12) from an open state toward a closed state when platform (618) is positioned between jaws (16, 18). In this regard, lever arms (622) may be sized and configured relative to end effector (12) such that closure surfaces (624) are collectively capable of at least partially circumferentially surrounding or encircling end effector (12) and to be in contact or near-contact with respective outer external surfaces of jaws (16, 18) for constricting end effector (12) in the closed state. For example, closure surfaces (624) may collectively define a variable cross dimension capable of being substantially equal to or slightly greater than a distance between outer external surfaces of jaws (16, 18) when end effector (12) is in the closed state. In one example, hinge pins (623) may be spaced apart from each other by a distance substantially equal to or slightly greater than the distance between outer external surfaces of jaws (16, 18) when end effector (12) is in the closed state.

Figure 21A:
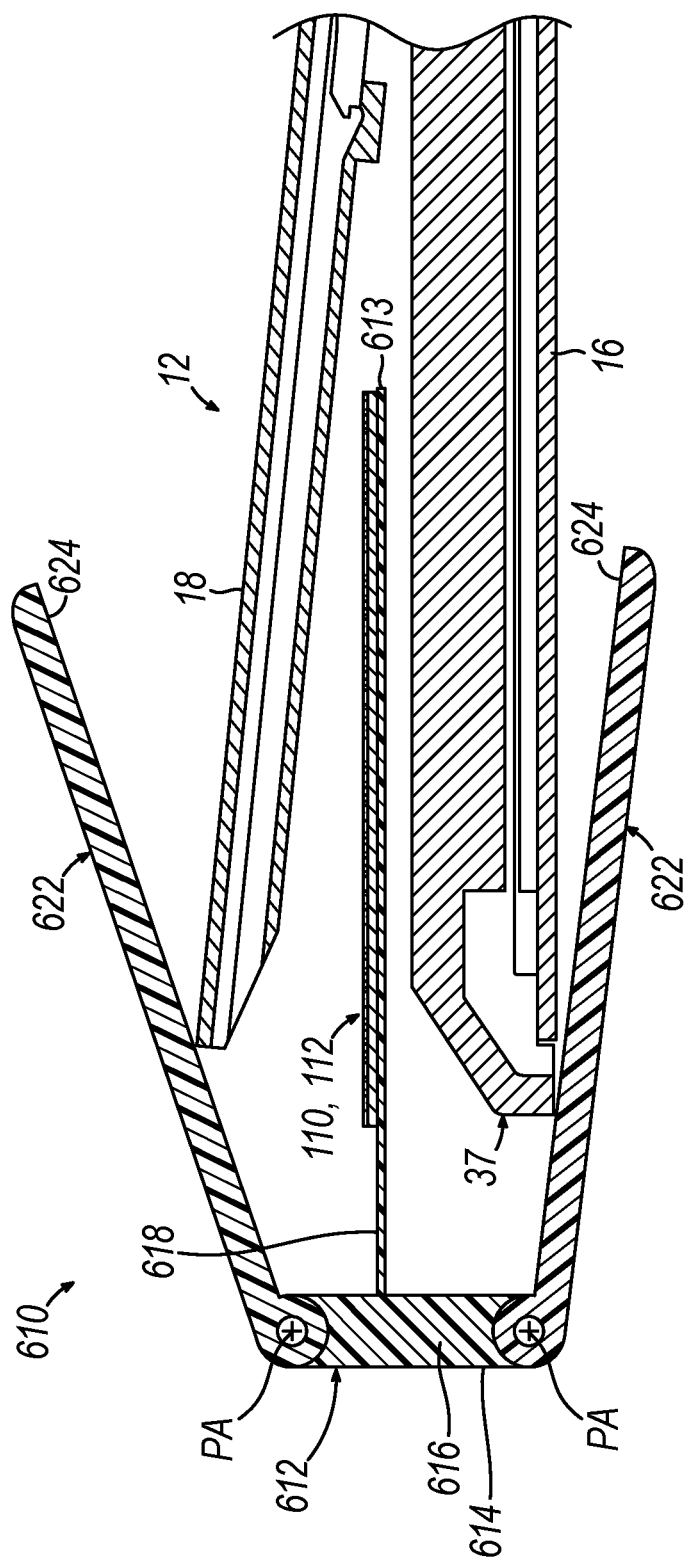
FIG. 21A depicts a side cross-sectional view of the buttress applicator of FIG. 20 positioned over the end effector of FIG. 3, showing pivotable lever arms of the buttress applicator in an open position.
Figure 21B:
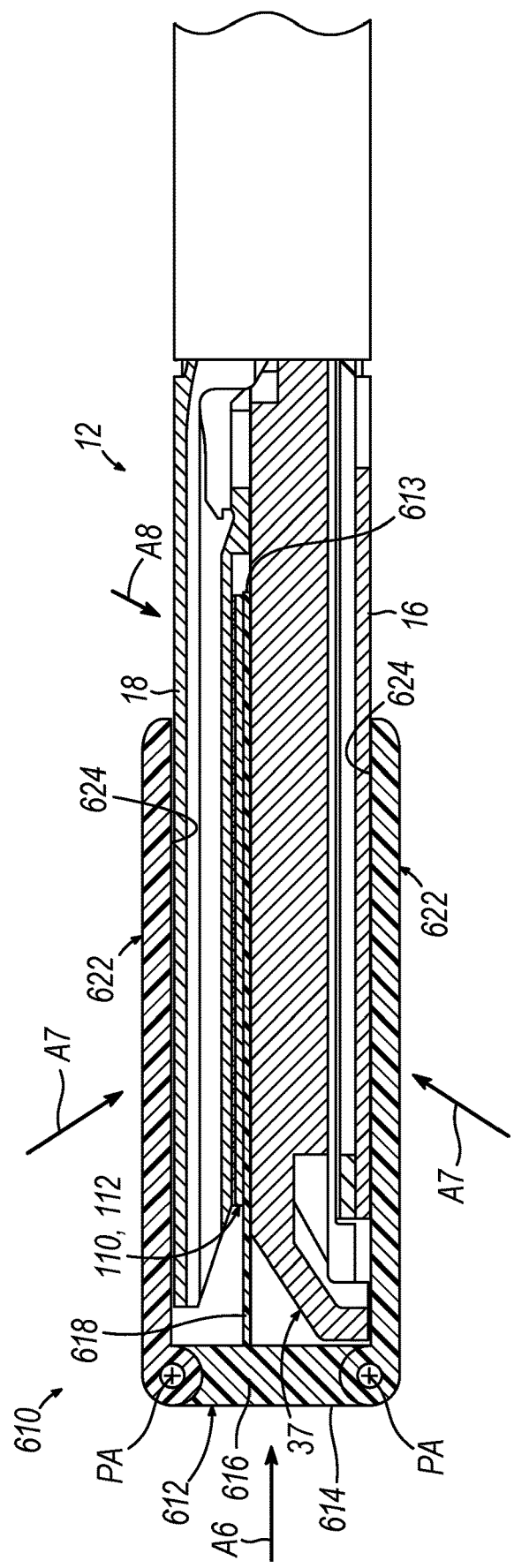
FIG. 21B depicts a side cross-sectional view of the buttress applicator of FIG. 20 positioned over the end effector of FIG. 3, showing the pivotable lever arms of the buttress applicator in a closed position for transitioning the end effector toward the closed state.

FIG. 21A shows buttress applicator (610) in a configuration where lever arms (622) are pivoted about the respective pivot axes (PA) from an open position toward a closed position such that closure surfaces (624) mechanically engage the outer external surfaces of the respective jaws (16, 18) to thereby transition end effector (12) from the open state toward the closed state; while FIG. 21B shows buttress applicator (610) in a configuration where lever arms (622) are in the closed position such that closure surfaces (624) mechanically engage the outer external surfaces of the respective jaws (16, 18) to thereby maintain end effector (12) in the closed state. To use buttress applicator (610) to load end effector (12), the operator would first position buttress applicator (610) and end effector (12) such that platform (618) and buttress assembly (110, 112) are positioned between anvil (18) and staple cartridge (37) and such that end effector (12) is received between lever arms (622) with lever arms (622) at or near the open position as shown in FIG. 21A. The operator would then advance buttress applicator (610) proximally relative to end effector (12) as indicated by sixth arrow (A6) in FIG. 21B and/or pivot lever arms (622) toward the closed position (e.g., by pinching lever arms (622) toward each other) as indicated by seventh arrows (A7) in FIG. 21B to mechanically engage closure surfaces (624) with the outer external surfaces of the respective jaws (16, 18) until closure surfaces (624) are generally parallel to the respective outer external surfaces as shown in FIG. 21B. End effector jaws (16, 18) may be back-driven closed on platform (618) by such mechanical engagement (e.g., while closure trigger (26) of instrument (10) remains unactuated) as indicated by eighth arrow (A8) in FIG. 21B, thereby adhesively attaching buttress assembly (110, 112) to anvil (18) (e.g., to the stapling surface thereof). Buttress assembly (110, 112) may be released from platform (618), such that end effector jaws (16, 18) may be disengaged from platform (618) while buttress assembly (110, 112) remains adhered to anvil (18), such as by pivoting lever arms (622) toward the open position. In one example, buttress applicator (610) may be simultaneously advanced proximally relative to end effector (12) while lever arms (622) are pivoted toward the closed position.

While buttress applicator (610) is shown applying buttress assembly (110, 112) to anvil (18), buttress applicator (610) may additionally or alternatively apply buttress assembly (110, 112) to lower jaw (16), such as to stapler cartridge (37) (e.g., to the stapling surface thereof).

In one example, buttress applicator (610) may include a threshold force-application or pressure-application feature configured to prevent the end effector jaws (16, 18) from pivoting toward the open state until lever arms (622) have applied a threshold force and/or pressure to the respective jaws (16, 18) sufficient to ensure proper seating of buttress assembly (110, 112) on anvil (18) (or lower jaw (16)). For example, each lever arm (622) may include one or more notches configured to frictionally engage the respective jaws (16, 18) for inhibiting opening of jaws (16, 18) until lever arms (622) are pivoted toward the open position. In addition or alternatively, buttress applicator (610) may include a threshold force-notification or pressure-notification feature configured to provide a visual, haptic, and/or audible indication to a user that lever arms (622) have applied a threshold force and/or pressure to the respective jaws (16, 18) sufficient to ensure proper seating of buttress assembly (110, 112) on anvil (18) (or lower jaw (16)).

E. Exemplary Buttress Applicator With Camming Lever Arm for Back-Driving End Effector Jaws FIG. 22 shows another exemplary buttress applicator (710) configured to force the jaws of an end effector to close onto a portion of buttress applicator (710) supporting one or more buttress assemblies (110, 112), or otherwise "back-drive" the jaws of the end effector for applying buttress assemblies (110, 112) thereon. Buttress applicator (710) is similar to buttress applicators (210, 310, 410, 510, 610) described above except as otherwise described below.

Buttress applicator (710) of this example comprises a frame (712) extending between a proximal end (not shown) and a distal end (714). Frame (712) includes a hinge knuckle (716) positioned at or near distal end (714) of frame (712), a compression pad or platform (718) extending proximally from knuckle (716) to the proximal end of frame (712), and a fixed arm (720) extending proximally from knuckle (716). Buttress applicator (710) further comprises a movable member in the form of a pivotable lever arm (722) coupled to knuckle (716) via a hinge pin (723) and configured to pivot relative to platform (718) about a lateral pivot axis (PA) extending in a direction perpendicular to a longitudinal axis of platform (718), and to selectively receive end effector (12) against fixed arm (720) as will be described in greater detail below.

Platform (718) of the present example is configured to support at least one buttress assembly (110, 112) on at least one side of platform (718). In the example shown, platform (718) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively. While platform (718) is shown supporting buttress assembly (110, 112) on only a single side of platform (718), platform (718) may just as easily support buttress assemblies (110, 112) on both sides of platform (718).

Lever arm (722) is generally flat and includes a protruding tapered closure surface (724) configured to selectively mechanically engage an outer external surface of one of end effector jaws (16, 18), while fixed arm (720) is generally flat and includes a generally flat untapered closure surface (726) configured to selectively mechanically engage an outer surface of the other of end effector jaws (16, 18) to thereby transition end effector (12) from an open state toward a closed state when platform (718) is positioned between jaws (16, 18). In this regard, arms (720, 722) may be sized and configured relative to end effector (12) such that closure surfaces (724, 726) are collectively capable of at least partially circumferentially surrounding or encircling end effector (12) and to be in contact or near-contact with respective outer external surfaces of jaws (16, 18) for constricting end effector (12) in the closed state. For example, closure surfaces (724, 726) may collectively define a variable cross dimension capable of being substantially equal to or slightly greater than a distance between outer external surfaces of jaws (16, 18) when end effector (12) is in the closed state. It will be appreciated that tapered closure surface (724) may alternatively be curved.

Figure 22A:
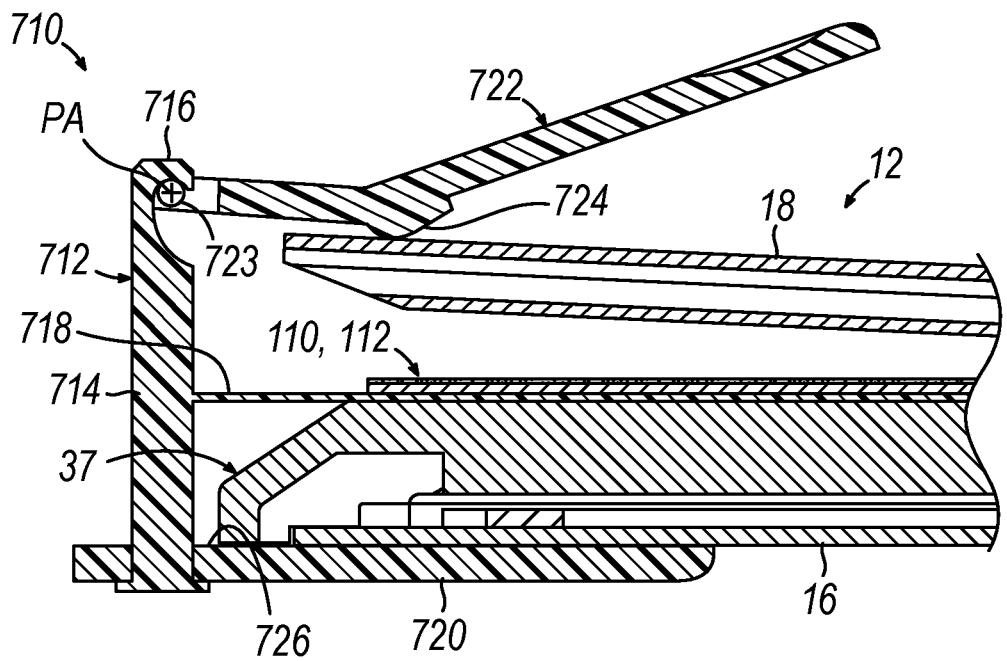
FIG. 22A depicts a side cross-sectional view of another exemplary buttress applicator that may be used to carry and apply the buttress assemblies of FIG. 8 positioned over the end effector of FIG. 3, showing a pivotable lever arm of the buttress applicator in an unactuated position.
Figure 22B:
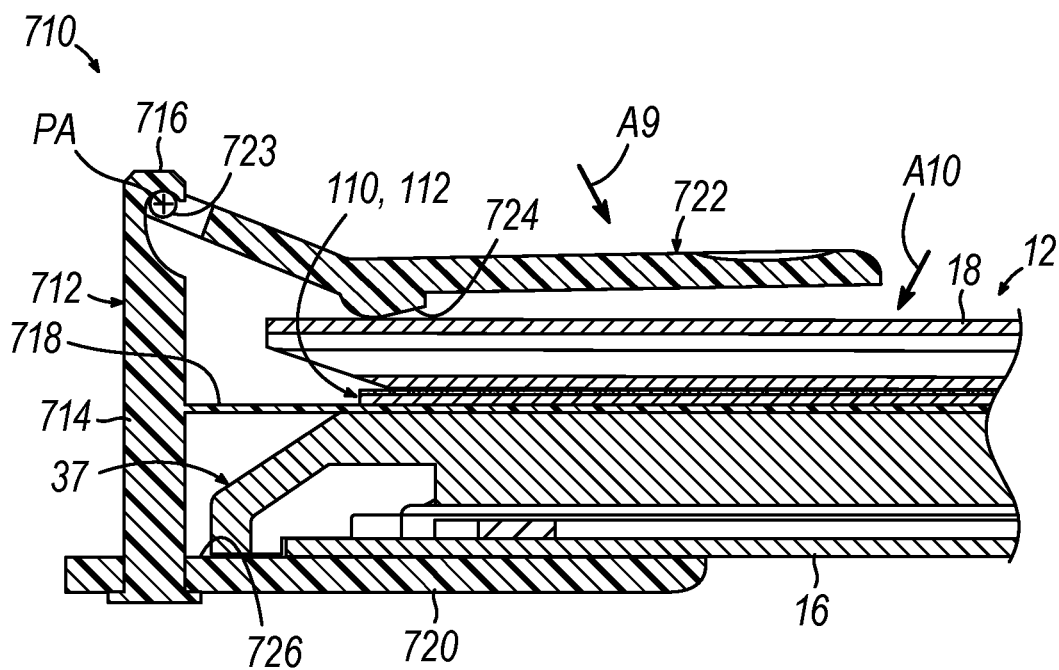
FIG. 22B depicts a side cross-sectional view of the buttress applicator of FIG. 22A positioned over the end effector of FIG. 3, showing the pivotable lever arm of the buttress applicator in an actuated position for transitioning the end effector toward the closed state.

FIG. 22A shows buttress applicator (710) in a configuration where lever arm (722) is pivoted about the pivot axis (PA) from an open position toward a closed position such that tapered closure surface (724) mechanically engages the outer external surface of anvil (18) while untapered closure surface (726) mechanically engages the outer external surface of lower jaw (16) to thereby transition end effector (12) from the open state toward the closed state; while FIG. 22B shows buttress applicator (710) in a configuration where lever arm (722) is in the closed position such that closure surfaces (724, 726) mechanically engage the respective outer external surfaces of jaws (16, 18) to thereby maintain end effector (12) in the closed state. To use buttress applicator (710) to load end effector (12), the operator would first position buttress applicator (710) and end effector (12) such that platform (718) and buttress assembly (110, 112) are positioned between anvil (18) and staple cartridge (37) and such that end effector (12) is received between arms (720, 722) with lever arm (722) at or near the open position as shown in FIG. 22A. The operator would then pivot lever arm (722) toward the closed position as indicated by ninth arrow (A9) in FIG. 22B to mechanically engage closure surface (724) with the outer external surface of anvil (18) such that anvil (18) is cammed radially inwardly as indicated by tenth arrow (A10) in FIG. 22B. End effector jaws (16, 18) may be back-driven closed on platform (718) by such mechanical engagement (e.g., while closure trigger (26) of instrument (10) remains unactuated) as shown in FIG. 22B, thereby adhesively attaching buttress assembly (110, 112) to anvil (18) (e.g., to the stapling surface thereof). Buttress assembly (110, 112) may be released from platform (718), such that end effector jaws (16, 18) may be disengaged from platform (718) while buttress assembly (110, 112) remains adhered to anvil (18). In one example, buttress applicator (710) may be simultaneously advanced proximally relative to end effector (12) while lever arm (722) is pivoted toward the closed position.

While buttress applicator (710) is shown applying buttress assembly (110, 112) to anvil (18), buttress applicator (710) may additionally or alternatively apply buttress assembly (110, 112) to lower jaw (16), such as to stapler cartridge (37) (e.g., to the stapling surface thereof).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus for applying at least one adjunct element to at least one of opposing first and second jaws of an end effector of a surgical stapler, wherein each of the first and second jaws includes a stapling surface and an external surface opposed from the respective stapling surface, the apparatus comprising: (a) a platform configured to be positioned between the first and second jaws of the end effector; (b) at least one adjunct element positioned on the platform; and (c) at least one closure surface opposed from the platform, wherein the at least one closure surface is configured to mechanically engage the external surface of at least one of the first or second jaws to thereby transition the end effector from an open state toward a closed state for placing the respective stapling surface of the at least one of the first or second jaws in contact with the at least one adjunct element.

EXAMPLE 2

The apparatus of Example 1, wherein the at least one closure surface is movable relative to the platform.

EXAMPLE 3

The apparatus of Example 2, further comprising: (a) an elongate rail fixedly coupled to the platform; and (b) a sleeve translatable along the elongate rail, wherein the at least one closure surface is presented by the sleeve.

EXAMPLE 4

The apparatus of Example 3, wherein when the platform is positioned between the first and second jaws, the sleeve is translatable along the elongate rail between a retracted position in which the at least one closure surface is mechanically disengaged from the external surface of the at least one of the first or second jaws and an extended position in which the at least one closure surface mechanically engages the external surface of the at least one of the first or second jaws to thereby transition the end effector from the open state toward the closed state.

EXAMPLE 5

The apparatus of any one or more of Examples 3 through 4, wherein the sleeve has a generally C-shaped cross section.

EXAMPLE 6

The apparatus of Example 2, further comprising a sleeve rotatable about an axis of rotation parallel to a longitudinal axis of the platform, wherein the at least one closure surface is presented by the sleeve.

EXAMPLE 7

The apparatus of Example 6, wherein when the platform is positioned between the first and second jaws, the sleeve is rotatable about the axis of rotation between a first angular position in which the at least one closure surface is mechanically disengaged from the external surface of the at least one of the first or second jaws and a second angular position in which the at least one closure surface mechanically engages the external surface of the at least one of the first or second jaws to thereby transition the end effector from the open state toward the closed state.

EXAMPLE 8

The apparatus of any one or more of Examples 6 through 7, wherein the sleeve includes a bore defining the at least one closure surface, wherein the bore has a generally oval cross section.

EXAMPLE 9

The apparatus of Example 2, further comprising at least one lever arm pivotable about a lateral axis extending in a direction perpendicular to a longitudinal axis of the platform, wherein the at least one closure surface is presented by the at least one lever arm.

EXAMPLE 10

The apparatus of Example 9, wherein when the platform is positioned between the first and second jaws, the at least one lever arm is pivotable about the lateral axis between an open position in which the at least one closure surface is mechanically disengaged from the external surface of the at least one of the first or second jaws and a closed position in which the at least one closure surface mechanically engages the external surface of the at least one of the first or second jaws to thereby transition the end effector from the open state toward the closed state.

EXAMPLE 11

The apparatus of any one or more of Examples 9 through 10, wherein the at least one closure surface is generally flat.

EXAMPLE 12

The apparatus of any one or more of Examples 9 through 11, wherein the at least one lever arm includes opposing first and second lever arms, wherein the at least one closure surface includes a first closure surface presented by the first lever arm and a second closure surface presented by the second lever arm.

EXAMPLE 13

The apparatus of any one or more of Examples 9 through 12, wherein the at least one closure surface includes at least one of a curved camming surface or a tapered camming surface.

EXAMPLE 14

The apparatus of Example 1, wherein the at least one closure surface is fixed against movement relative to the platform.

EXAMPLE 15

The apparatus of Example 14, wherein the at least one closure surface includes at least one of a curved camming surface or a tapered camming surface.

EXAMPLE 16

A system comprising: (a) an end effector of a surgical stapler, wherein the end effector includes opposing first and second jaws, wherein each of the first and second jaws includes a stapling surface and an external surface opposed from the respective stapling surface; and (b) the apparatus of any one or more of Examples 1 through 15.

EXAMPLE 17

The system of Example 16, wherein the platform of the apparatus is positioned between the first and second jaws of the end effector.

EXAMPLE 18

An apparatus for applying at least one adjunct element to at least one of opposing first and second jaws of an end effector of a surgical stapler, wherein each of the first and second jaws includes a stapling surface and an external surface opposed from the respective stapling surface, the apparatus comprising: (a) a platform configured to be positioned between the first and second jaws of the end effector; (b) at least one adjunct element positioned on the platform; and (c) at least one closure surface opposed from the platform, wherein the at least one closure surface is configured to move relative to the external surface of at least one of the first or second jaws when the platform is positioned between the first and second jaws to thereby transition the end effector from an open state toward a closed state for placing the respective stapling surface of the at least one of the first or second jaws in contact with the at least one adjunct element.

EXAMPLE 19

The apparatus of Example 18, further comprising at least one movable member, wherein the at least one closure surface is presented by the at least one movable member, wherein the at least one closure surface is configured to transition the end effector from the open state toward the closed state in response to movement of the movable member relative to the platform.

EXAMPLE 20

The apparatus of Example 18, wherein the at least one closure surface is configured to transition the end effector from the open state toward the closed state in response to translation of the end effector relative to the platform.

EXAMPLE 21

A system comprising: (a) an end effector of a surgical stapler, wherein the end effector includes opposing first and second jaws, wherein each of the first and second jaws includes a stapling surface and an external surface opposed from the respective stapling surface; and (b) the apparatus of any one or more of Examples 18 through 20.

EXAMPLE 22

The system of Example 21, wherein the platform of the apparatus is positioned between the first and second jaws of the end effector.

EXAMPLE 23

A method of securing an adjunct element to an end effector of a surgical stapler having opposing first and second jaws, wherein each of the first and second jaws includes a stapling surface and an external surface opposed from the respective stapling surface, the method comprising: (a) positioning a platform of an adjunct element applicator between the first and second jaws, wherein the adjunct element is disposed on the platform; and (b) transitioning the end effector from an open state toward a closed state by mechanically engaging at least one closure surface of the adjunct element applicator with the external surface of at least one of the first or second jaws to thereby place the respective stapling surface of the at least one of the first or second jaws in contact with the at least one adjunct element.

EXAMPLE 24

The method of Example 23, wherein the end effector includes a closure system configured to selectively transition the end effector from the open state toward the closed state, wherein the step of transitioning the end effector from the open state toward the closed state is performed while maintaining the closure system of the end effector in an unactuated state.

EXAMPLE 25

The method of any one or more of Examples 23 through 24, wherein transitioning the end effector from the open state toward the closed state includes moving the at least one closure surface relative to the platform.

EXAMPLE 26

The method of Example 25, wherein the adjunct element applicator includes (a) an elongate rail fixedly coupled to the platform, and (b) a sleeve, wherein the at least one closure surface is presented by the sleeve, wherein transitioning the end effector from the open state toward the closed state includes translating the sleeve along the elongate rail.

EXAMPLE 27

The method of Example 26, wherein transitioning the end effector from the open state toward the closed state includes translating the sleeve along the elongate rail between a retracted position in which the at least one closure surface is mechanically disengaged from the external surface of the at least one of the first or second jaws and an extended position in which the at least one closure surface mechanically engages the external surface of the at least one of the first or second jaws to thereby transition the end effector from the open state toward the closed state.

EXAMPLE 28

The method of any one or more of Examples 26 through 27, wherein the sleeve has a generally C-shaped cross section.

EXAMPLE 29

The method of Example 25, wherein the adjunct element applicator includes a sleeve, wherein the at least one closure surface is presented by the sleeve, wherein transitioning the end effector from the open state toward the closed state includes rotating the sleeve about an axis of rotation parallel to a longitudinal axis of the platform.

EXAMPLE 30

The method of Example 29, wherein transitioning the end effector from the open state toward the closed state includes rotating the sleeve about the axis of rotation between a first angular position in which the at least one closure surface is mechanically disengaged from the external surface of the at least one of the first or second jaws and a second angular position in which the at least one closure surface mechanically engages the external surface of the at least one of the first or second jaws to thereby transition the end effector from the open state toward the closed state.

EXAMPLE 31

The method of any one or more of Examples 29 through 30, wherein the sleeve includes a bore defining the at least one closure surface, wherein the bore has a generally oval cross section.

EXAMPLE 32

The method of Example 25, wherein the adjunct element applicator includes at least one lever arm, wherein the at least one closure surface is presented by the at least one lever arm, wherein transitioning the end effector from the open state toward the closed state includes pivoting the at least one lever arm about a lateral axis extending in a direction perpendicular to a longitudinal axis of the platform.

EXAMPLE 33

The method of Example 32, wherein transitioning the end effector from the open state toward the closed state includes pivoting the at least one lever arm about the lateral axis between an open position in which the at least one closure surface is mechanically disengaged from the external surface of the at least one of the first or second jaws and a closed position in which the at least one closure surface mechanically engages the external surface of the at least one of the first or second jaws to thereby transition the end effector from the open state toward the closed state.

EXAMPLE 34

The method of any one or more of Examples 32 through 33, wherein the at least one closure surface is generally flat.

EXAMPLE 35

The method of any one or more of Examples 32 through 34, wherein the at least one lever arm includes opposing first and second lever arms, wherein the at least one closure surface includes a first closure surface presented by the first lever arm and a second closure surface presented by the second lever arm.

EXAMPLE 36

The method of any one or more of Examples 32 through 35, wherein the at least one closure surface includes at least one of a curved camming surface or a tapered camming surface.

EXAMPLE 37

The method of any one or more of Examples 23 through 24, wherein transitioning the end effector from the open state toward the closed state includes maintaining the at least one closure surface fixed against movement relative to the platform.

EXAMPLE 38

The apparatus of Example 37, wherein the at least one closure surface includes at least one of a curved camming surface or a tapered camming surface.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/022,186, entitled "Apparatus and Method to Apply Buttress to End Effector of Surgical Stapler via Fixed Base," filed on Sep. 16, 2020, published as U.S. Pub. No. 2022/0079592 on Mar. 17, 2022; U.S. patent application Ser. No. 17/022,209, entitled "Apparatus and Method to Apply Buttress to End Effector of Surgical Stapler via Driven Member," filed on Sep. 16, 2020, published as U.S. Pub. No. 2022/0079580 on Mar. 17, 2022; U.S. patent application Ser. No. 17/022,214, entitled "Apparatus and Method to Apply Buttresses Separately to Jaws of End Effector of Surgical Stapler," filed on Sep. 16, 2020, published as U.S. Pub. No. 2022/0079581 on Mar. 17, 2022; U.S. patent application Ser. No. 17/022,419, entitled "Apparatus and Method to Detect Full Seating of Buttress Applicator in End Effector of Surgical Stapler," filed on Sep. 16, 2020, published as U.S. Pub. No. 2022/0079587 on Mar. 17, 2022; U.S. patent application Ser. No. 17/022,442, entitled "Apparatus and Method to Apply Buttress to End Effector of Surgical Stapler with Authentication," filed on Sep. 16, 2020, published as U.S. Pub. No. 2022/0079584 on Mar. 17, 2022; and/or U.S. patent application Ser. No. 17/022,520, entitled "Method of Applying Buttress to End Effector of Surgical Stapler," filed on Sep. 16, 2020, published as U.S. Pub. No. 2022/0079593 on Mar. 17, 2022. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for applying at least one adjunct element to at least one of opposing first and second jaws of an end effector of a surgical stapler, wherein each of the first and second jaws includes a stapling surface and an external surface opposed from the respective stapling surface, the apparatus comprising:
   (a) a platform configured to be positioned between the first and second jaws of the end effector;
   (b) at least one adjunct element positioned on the platform; and
   (c) at least one closure element coupled to the platform, wherein the at least one closure element includes at least one closure surface opposed from the platform, wherein the at least one closure surface is configured to mechanically engage the external surface of at least one of the first or second jaws to thereby transition the end effector from an open state toward a closed state for placing the respective stapling surface of the at least one of the first or second jaws in contact with the at least one adjunct element.

2. The apparatus of claim 1, wherein the at least one closure surface is movable relative to the platform.

3. The apparatus of claim 2, further comprising:
   (a) an elongate rail fixedly coupled to the platform;
   wherein the at least one closure element includes a sleeve translatable along the elongate rail, wherein the at least one closure surface is included in the sleeve.

4. The apparatus of claim 3, wherein when the platform is positioned between the first and second jaws, the sleeve is translatable along the elongate rail between a retracted position in which the at least one closure surface is mechanically disengaged from the external surface of the at least one of the first or second jaws and an extended position in which the at least one closure surface mechanically engages the external surface of the at least one of the first or second jaws to thereby transition the end effector from the open state toward the closed state.

5. The apparatus of claim 3, wherein the sleeve has a generally C-shaped cross section.

6. The apparatus of claim 2, wherein the at least one closure element includes a sleeve rotatable about an axis of rotation parallel to a longitudinal axis of the platform, wherein the at least one closure surface is included in the sleeve.

7. The apparatus of claim 6, wherein when the platform is positioned between the first and second jaws, the sleeve is rotatable about the axis of rotation between a first angular position in which the at least one closure surface is mechanically disengaged from the external surface of the at least one of the first or second jaws and a second angular position in which the at least one closure surface mechanically engages the external surface of the at least one of the first or second jaws to thereby transition the end effector from the open state toward the closed state.

8. The apparatus of claim 6, wherein the sleeve includes a bore defining the at least one closure surface, wherein the bore has a generally oval cross section.

9. The apparatus of claim 2, wherein the at least one closure element includes at least one lever arm pivotable about a lateral axis extending in a direction perpendicular to a longitudinal axis of the platform, wherein the at least one closure surface is included in the at least one lever arm.

10. The apparatus of claim 9, wherein when the platform is positioned between the first and second jaws, the at least one lever arm is pivotable about the lateral axis between an open position in which the at least one closure surface is mechanically disengaged from the external surface of the at least one of the first or second jaws and a closed position in which the at least one closure surface mechanically engages the external surface of the at least one of the first or second jaws to thereby transition the end effector from the open state toward the closed state.

11. The apparatus of claim 9, wherein the at least one closure surface is generally flat.

12. The apparatus of claim 9, wherein the at least one lever arm includes opposing first and second lever arms, wherein the at least one closure surface includes a first closure surface included in the first lever arm and a second closure surface included in the second lever arm.

13. The apparatus of claim 9, wherein the at least one closure surface includes at least one of a curved camming surface or a tapered camming surface.

14. The apparatus of claim 1, wherein the at least one closure surface is fixed against movement relative to the platform.

15. The apparatus of claim 14, wherein the at least one closure surface includes at least one of a curved camming surface or a tapered camming surface.

16. The apparatus of claim 1, wherein the at least one closure surface is configured to mechanically engage the external surface of the at least one of the first or second jaws to thereby transition the end effector from the open state toward the closed state independently of a closure system of the end effector.

17. An apparatus for applying at least one adjunct element to at least one of opposing first and second jaws of an end effector of a surgical stapler, wherein each of the first and second jaws includes a stapling surface and an external surface opposed from the respective stapling surface, the apparatus comprising:
   (a) a platform configured to be positioned between the first and second jaws of the end effector;
   (b) at least one adjunct element positioned on the platform; and
   (c) at least one closure element coupled to the platform, wherein the at least one closure element includes at least one closure surface opposed from the platform, wherein the at least one closure surface is configured to move relative to the external surface of at least one of the first or second jaws when the platform is positioned between the first and second jaws to thereby transition the end effector from an open state toward a closed state for placing the respective stapling surface of the at least one of the first or second jaws in contact with the at least one adjunct element.

18. The apparatus of claim 17, wherein the at least one closure element includes at least one movable member, wherein the at least one closure surface is included in the at least one movable member, wherein the at least one closure surface is configured to transition the end effector from the open state toward the closed state in response to movement of the movable member relative to the platform.

19. The apparatus of claim 17, wherein the at least one closure surface is configured to transition the end effector from the open state toward the closed state in response to translation of the end effector relative to the platform.

20. A method of securing an adjunct element to an end effector of a surgical stapler having opposing first and second jaws, wherein each of the first and second jaws includes a stapling surface and an external surface opposed from the respective stapling surface, the method comprising:

(a) positioning a platform of an adjunct element applicator between the first and second jaws, wherein the adjunct element is disposed on the platform; and (b) transitioning the end effector from an open state toward a closed state by mechanically engaging at least one closure surface of at least one closure element of the adjunct element applicator with the external surface of at least one of the first or second jaws to thereby place the respective stapling surface of the at least one of the first or second jaws in contact with the at least one adjunct element, wherein the end effector includes a closure system configured to selectively transition the end effector from the open state toward the closed state, wherein the step of transitioning the end effector from the open state toward the closed state is performed while maintaining the closure system of the end effector in an unactuated state.

* * * * *